United States Patent [19]

Hsu

[11] 4,159,262

[45] Jun. 26, 1979

[54] CATALYTIC TRIMERIZATION OF AROMATIC NITRILES AND TRIARYL-s-TRIAZINE RING CROSS-LINKED HIGH TEMPERATURE RESISTANT POLYMERS AND COPOLYMERS MADE THEREBY

[75] Inventor: Li-Chen Hsu, Cleveland, Ohio

[73] Assignee: The United States of America as represented by the Administrator, National Aeronautics and Space Administration, Washington, D.C.

[21] Appl. No.: 796,263

[22] Filed: May 12, 1977

Related U.S. Application Data

[62] Division of Ser. No. 513,613, Oct. 10, 1974, Pat. No. 4,061,856.

[51] Int. Cl.$^2$ ............... C08G 73/10; C07D 251/00
[52] U.S. Cl. ............... 528/126; 260/37 N; 260/42; 260/53; 544/193; 528/221; 528/223; 528/229; 528/227; 528/225; 528/127; 528/128; 528/336; 528/337; 528/338; 528/342; 528/331
[58] Field of Search ............... 260/78.41, 2 R, 42.53, 260/37 N, 248 CS; 544/193

[56] References Cited

U.S. PATENT DOCUMENTS

| | | | |
|---|---|---|---|
| 3,060,179 | 10/1962 | Toland | 260/248 |
| 3,164,555 | 1/1965 | Karguin et al. | 260/2 |
| 3,470,176 | 9/1969 | Zollinger | 260/248 |
| 3,502,579 | 3/1970 | Johns et al. | 252/12 |
| 3,518,264 | 6/1970 | Beears | 260/248 |
| 3,560,444 | 2/1971 | DeBrunner | 260/65 |
| 3,595,971 | 7/1971 | Behr | 260/47 R |
| 3,644,286 | 2/1972 | Odier | 260/78.41 X |
| 3,654,192 | 4/1972 | Vogel | 260/2 R |
| 3,655,632 | 4/1972 | Ohfuji et al. | 260/78.41 |
| 3,804,804 | 4/1974 | Gerber et al. | 260/78.41 X |
| 3,809,693 | 5/1974 | Miller | 260/248 |
| 3,943,107 | 3/1976 | Seitzer et al. | 260/78.41 X |
| 3,993,631 | 11/1976 | Griffith et al. | 260/78.41 X |

*Primary Examiner*—John Kight, III
*Attorney, Agent, or Firm*—Norman T. Musial; John R. Manning; James A. Mackin

[57] ABSTRACT

Triazine compounds and cross-linked polymer compositions are made by heating aromatic nitriles to a temperature in the range of from about 100° C. to about 700° C., and preferably in the range of from about 200° C. to about 350° C. in the presence of a catalyst or mixture of catalysts selected from one or more of the following groups: (A) organic sulfonic and sulfinic acids, (B) organic phosphonic and phosphinic acids, and (C) metallic acetylacetonates, at a pressure in the range of from about atmospheric pressure to about 10,000 p.s.i., and preferably in the range of from about 200 p.s.i. to about 750 p.s.i.

Aromatic nitrile-modified (terminated and/or appended) imide, benzimidazole, imidazopyrrolone, quinoxaline, and other condensation type prepolymers or their precopolymers are made which are trimerized with or without a filler by the aforementioned catalytic trimerization process into triaryl-s-triazine ring containing or cross-linked polymeric or copolymeric products useful in applications requiring high thermal-oxidative stability and high performance structural properties at elevated temperatures.

23 Claims, No Drawings

CATALYTIC TRIMERIZATION OF AROMATIC NITRILES AND TRIARYL-S-TRIAZINE RING CROSS-LINKED HIGH TEMPERATURE RESISTANT POLYMERS AND COPOLYMERS MADE THEREBY

ORIGIN OF THE INVENTION:

The invention described herein was made by an employee of the United States Government and may be manufactured and used by or for the Government for governmental purposes without the payment or any royalties thereon or therefor.

BACKGROUND OF THE INVENTION

1. Field of the Invention

The invention relates to a novel process for preparing triaryl-s-triazines from aromatic nitriles, and triaryl-s-triazine ring containing or cross-linked polymers or copolymers from aromatic nitrile-modified (terminated and/or appended) prepolymers or precopolymers in the presence of a novel catalyst and relates to the novel compounds and polymers produced by the above process. More particularly, the invention relates to the use of the novel process, polymers and compounds to produce fiber-reinforced composites of outstanding thermal-oxidative stability.

2. Description of the Prior Art

Conventional condensation-type aromatic polyimides, polybenzimidazoles, polvimidazopyrrolones, and polyquinoxalines exhibit excellent thermal-oxidative stability, but they are, however, difficult to process into fiber-reinforced composites. Various workers have attempted to solve the processability problem of these high temperature resistant polymers with varying degrees of success.

Prior to the present invention, aromatic nitriles were trimerized at a temperature in the range of 350° C. to 500° C. and under a pressure of 35,000 to 50,000 atmospheres. Bengelsdorf, I. S., "High Pressure High Temperature Reactions. I. The Trimerization of Aromatic Nitriles", J. Amer. Chem. Soc., Vol. 80, p. 803 (1958). In U.S. Pat. No. 2,503,999, Cairns et al. trimerized aromatic nitriles at a temperature in the range of 60° C. to 150° C. and under a pressure above 3,000 atmospheres with an alcohol catalyst. In U.S. Pat. No. 1,989,042, Kunz et al. trimerized aromatic nitriles below room temperature with chlorosulfonic acid served as both the solvent and catalyst. In U.S. Pat. No. 2,598,811, Mahan et al. trimerized aromatic nitriles at a temperature in the range of 66° C. to 288° C. and under a pressure in the range of 30 p.s.i. to 500 p.s.i. with a catalyst selected from the groups consisting of hydrides and amides of alkali metals, and hydrides of alkaline earth metals. In U.S. Pat. No. 3,095,414, Spainhour synthesized triazines at a temperature in the range of 25° C. to 150° C. in a sealed reactor with a catalyst mixture selected from one group consisting of metallic salts such as titanium tetrachloride and another group consisting of organometallic compounds such as trialkyl aluminum. In U.S. Pat. No. 3,060,179, Toland polymerized aromatic nitriles at a temperature in the range of 200° C. to 400° C. in an open or pressure vessel with a metal salt catalyst selected from the group consisting of copper, manganese, and cobalt. In U.S. Pat. No. 3,678,049, Gump polymerized aromatic nitriles at a temperature in the range of 200° C. to 350° C. in an autoclave under an initial pressure of about 0.001 mm of Hg with 2-pyrrolidinone served as both the catalyst and solvent. Because of either the superhigh pressure required or the quantity and particularly the nature of catalyst used, none of the trimerization methods previously described are suitable for processing the aromatic nitrile-modified (terminated and/or appended) condensation type prepolymers into a s-triazine ring cross-linked high temperature resistant matrix resins for fiber reinforced composites.

Prior to the present invention, Lubowitz, in U.S. Pat. No. 3,528,950, developed a new system of processable thermally stable modified polyimides as matrices for fiber-reinforced composites. These processable modified polyimides, known as addition-type polyimides were made from imide oligomers terminated with norbornene groups. After removal of the solvent, these norbornene-terminated imide oligomers can be polymerized and/or cross-linked by an addition reaction primarily through the double bonds to yield thermally stable polyimides without the evolution of by-products. Fiber-reinforced composites made from these norbernene-terminated polyimides, however, cannot reach an upper service temperature of about 315° C. This is apparently due to the presence of the aliphatic cyclic structure derived from the norbornene groups.

SUMMARY OF THE INVENTION

The disadvantages and limitations of the prior art are alleviated by the present invention. In accordance with the present invention, aromatic nitriles such as p-cyanobenzoic acid and its esters, etc. can be directly trimerized to their corresponding triaryl-s-triazines at moderate temperature and pressure.

Further, in accordance with the present invention, the norbornene groups on the addition-type polyimides are replaced by aromatic nitrile groups, or part of the monomeric reactants (aromatic diamines and tetracarboxylic acid dianhydride or their derivatives) of those soluble high molecular weight polyimides having relatively low thermal stability were replaced by nitrile appended aromatic diamines and aromatic tetracarboxylic acid dianhydrides or their derivatives. These terminating and/or appending aromatic nitrile groups are then catalytically trimerized to produce new triaryl-s-triazine ring containing or cross-linked polyimides which possess the outstanding thermal stability of both polyimides and aryl-s-triazines for continuous use at temperatures above 315° C.

Since conventional fiber-reinforced composites are usually fabricated at temperatures in the range of 100° C. to 350° C. and under a pressure below 1000 p.s.i., it is an object of this invention to provide novel catalysts which not only effectively trimerize aromatic nitriles under these reaction conditions but also themselves possess reasonably good thermal and hydrolytic stabilities.

Also, in accordance with this invention, aromatic nitrile-modified (terminated and/or appended) benzimidazole, imidazopyrrolone, quinoxaline and other condensation type prepolymers or precopolymers can be catalytically trimerized to form triaryl-s-triazine ring cross-linked heat thermosetting polymeric products or filler-reinforced composites, particularly fiber-reinforced composites which exhibit good thermal-oxidative stability and high performance structural properties at elevated temperatures.

DESCRIPTION OF THE INVENTION

In accordance with the present invention, trimerizable aromatic nitrile compounds are trimerized to form triazine rings by heating such nitriles under substantially anhydrous conditions with a novel catalyst or a catalyst mixture selected from the group consisting of organic sulfonic and sulfinic acids, organic phosphonic and phosphinic acids, and metallic acetylacetonates.

The term "substantially anhydrous conditions" as used herein in reference to trimerization process conditions refers to the fact that the total amount of water present in a reaction zone is such that it does not appreciably interfere with production of triazine from the starting materials under a given set of reaction conditions.

Examples of organic sulfonic and sulfinic acids which are suitable as catalysts for use in the novel process of this invention included p-toluene sulfonic acid, benzene sulfonic acid, benzene sulfinic acid, naphthalene β-sulfonic acid and the like. Examples of organic phosphonic and phosphinic acids which are suitable as catalysts for use in the novel process of this invention include trichloromethyl phosphonic acid, phenyl phosphonic acid, phenyl phosphinic acid, and the like. For the two acid catalyst groups mentioned above, examples of suitable catalysts also include derivatives which generate the corresponding acids under the reaction conditions during processing. Examples of metallic acetylacetonates which are suitable as catalysts for use in the novel process of this invention include ferric acetylacetonate, zinc acetylacetonate, and the like.

In order to initiate and maintain the trimerization reaction, it is merely necessary that the amount of catalyst be sufficient, based on molar percentage of the nitrile employed. Except for practical purposes, there is no known maximum amount. However, since the catalyst normally would either have to be separated from or remain in the reaction product it normally would be desirable to employ as little catalyst as necessary to accomplish the desired result. As is readily apparent to one skilled in the art, the amount of catalyst used depends upon the specific catalyst that is employed. There would rarely be any need to employ higher than about 10 mole percent of catalyst based on the amount of nitrile employed. In general, the catalyst concentrations are within the range of about 0.01 mole percent to about 10.0 mole percent and the preferred range is from about 0.05 mole percent to about 5.0 mole percent based on the molar amount of nitrile employed.

Reaction times are not critical, but should preferably be of sufficient length to permit the trimerization reaction to be essentially completed. The reaction time is typically dependent on several factors such as the particular catalyst employed, the amount of catalyst employed, the temperature and pressure at which the reaction is carried out, the nitrile employed, and the degree of conversion desired. The time required for reaction of a given nitrile, catalyst and temperature combination varies depending especially upon the nitrile used in the reaction, but can be adjusted by control of the other process variables, such as equipment, reaction conditions, reactants, etc. A reaction time of from about a day to about three days is normally satisfactory.

Reaction pressures are also dependent on the nitrile, catalyst and temperature employed and are generally in the range of from about atmospheric to about 10,000 p.s.i., preferably in the range of from about 50 p.s.i. to about 1,000 p.s.i. and more preferably in the range of from about 200 p.s.i. to about 750 p.s.i. reaction is conveniently carried out in an inert atmosphere such as nitrogen if a pressure reactor is used.

The novel process of this invention for trimerizing aromatic nitrile compounds to the triaryl-s-triazines, and aromatic nitrile-modified prepolymers or precopolymers to triaryl-s-triazine ring containing or crosslinked polymers or copolymers is operable at a temperature in the range of from about 100° C. to about 700° C., preferably in the range of from about 100° C. to about 500° C. and more preferably in the range of from about 200° C. to about 350° C.

Sometimes it is desirable to employ an inert solvent, organic in nature, in which both the catalyst and the reactants are soluble. The inert solvent is preferably an organic liquid which is substantially unreactive with both the reactants and the reaction products and in which the reactants are soluble to a desired extent. It is generally preferable to choose one which is readily separated from the reaction products. Suitable solvents for the novel process of the present invention include N-methylpyrrolidone, N,N-dimethyl formamide, dimethylsulfoxide, cresols, alcohols, 1,2,-dichloroethane and the like depending on the monomeric reactants used and the chemical structure and molecular weight of the aromatic nitrile-modified prepolymers or precopolymers produced.

The novel process of this invention for trimerizing aromatic nitrile compounds to form triazine rings may be used generally to trimerize any conventional aromatic nitrile such as benzonitrile, napthonitrile, cyanoanthracene, and cyanoheterocyclic compounds which may be substituted with alkyl, alkoxy, halogen, nitro, cyano, carbonyl, sulfonyl, carboxyl groups, and the like.

As set forth in Table I below, benzonitrile with electron withdrawing ring substituents such as carboxyl and nitro groups was found to be more susceptible to trimerization than those with electron donating substituents such as methyl and methoxy groups, and that as expected the ortho substituted benzonitrile was less susceptible to trimerization than either para or meta substituted benzonitriles.

TABLE I

CATALYTIC TRIMERIZATION OF SUBSTITUTED BENZONITRILES

| Aromatic Nitrile | M.P. (°C.) | Trimerized Product Percent Yield | M.P. (°C.) |
|---|---|---|---|
| Anisonitrile | 55–56 | 6.0 | >340 (217 and 224*) |
| p-Tolunitrile | 26–28 | 5.0 | >340 (278-9*) |
| Benzonitrile | −14 | 14.0 | 232–235 (232-3*) |
| o-Nitrobenzonitrile | 102–106 | 37.8 | >340 |
| m-Nitrobenzonitrile | 117–118 | 51.6 | >340 (342*) |
| p-Nitrobenzonitrile | 146–149 | 52.3 | >340 (>360*) |
| 3,5-Dinitrobenzonitrile | 128–130 | 54.0 | 310 |
| p-Cyanobenzoic acid | 220–222 | 75.0 | >340 (374-5*) |
| Terephthalonitrile | 231 | 99.5 | >340 |

*Value in literature
Reaction conducted at 232° C., 600–750 p.s.i., for 48 hours, with 5 mole per cent p-toluenesulfonic acid catalyst.

In accordance with the present invention, aromatic nitrile compounds may be trimerized by the novel process of this invention to form triaryl-s-triazine compounds that are useful as cross-linking reagents for synthesizing high temperature resistant polymeric products. They may also be useful as intermediate compounds for synthesizing dyestuffs and drugs.

The triaryl-s-triazine compounds produced by the novel process of this invention include 2,4,6-tris (meta-, ortho- or para-carboxyphenyl)-1,3,5-triazine and its ester or halide derivatives, 2,4,6-tris (3',4'-phthalic anhydride)-1,3,5-triazine and its ester and halide derivatives, 2,4,6-tris (meta-, ortho- or para-aminophenyl)-1,3,5-triazine, 2,4,6-tris (3',4'-diaminophenyl)1,3,5-triazine, 2,4,6-tris (3',5'-diaminophenyl)-1,3,5-triazine, and 2,4,6-tris (meta- or para-substituted phthalimidyl)-1,3,5-triazine where the substituted groups are monovalent radicals selected from the group consisting of —H, —CN, —F, —Cl, —Br, —NO$_2$, —CH$_3$, —NH$_2$,

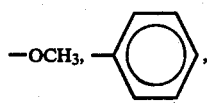

and substituted aryls.

The aromatic nitrile compounds that are trimerized in accordance with the present invention to produce the aforementioned triaryl-s-triazine compounds are aromatic carbocyclic nitriles selected from the group consisting of:

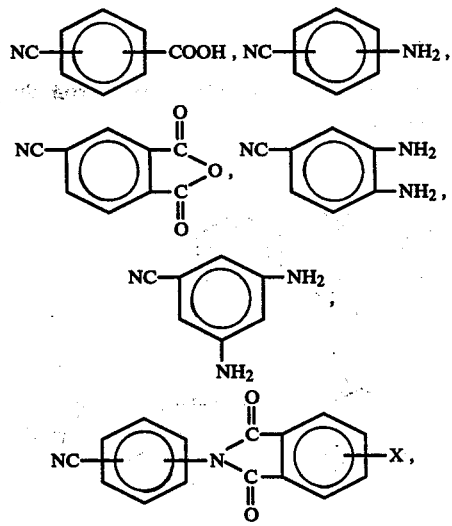

wherein X is a monovalent radical selected from the group consisting of —H, —CN, —F, —Cl, —Br, —NO$_2$, —CH$_3$, —NH$_2$, —OCH$_3$,

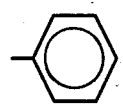

and substituted aryls, and X may be substituted at the meta and para positions.

The triaryl-s-triazine ring containing or cross-linked polymeric or copolymeric products produced by the novel process of this invention are typically useful in applications requiring high temperature stability and may be processed with filler reinforcement, particularly with fiber reinforcement to produce highly heat resistant molded articles.

Fillers suitable for reinforcement to preparing composites by the novel process of the present invention include graphite fibers such as Hercules' HMS graphite fibers, etc., high temperature resistant organic fibers such as Du Pont's Aramid fiber, etc., glass fibers with or without coated coupling finishes, glass, quartz, and other ceramic powders, certain metallic powders, whiskers, and wires having high temperature resistant stability.

In accordance with the present invention, novel aromatic nitrile-modified (terminated and/or appended) imide, benzimidazole, imidazopyrrolone, and quinoxaline prepolymers and aromatic dinitrile compounds including those aromatic nitrile-endcapped soluble polyarylenes, polyarylenesulfides, polyarylethers, polyarylketones, polyarylsulfones, polysiloxanes, and their copolymers may be trimerized to form neat resins or composites exhibiting good or outstanding thermal-oxidative stability and high performance structural properties.

The polyimide class of polymers are known to possess outstanding physical properties, notably a high degree of stability to heat as well as excellent mechanical properties of shaped articles which are fabricated from the polymers, such as films, fibers, laminates, moldings, and the like. According to the present invention, novel aromatic nitrile-modified imide prepolymers are disclosed which may be trimerized to form a new system of polyimides which possess the outstanding thermal stability of both polyimides and triaryl-s-triazines.

The novel processable aromatic nitrile-modified imide prepolymers made in accordance with the present invention have one of the following four general structural formulas:

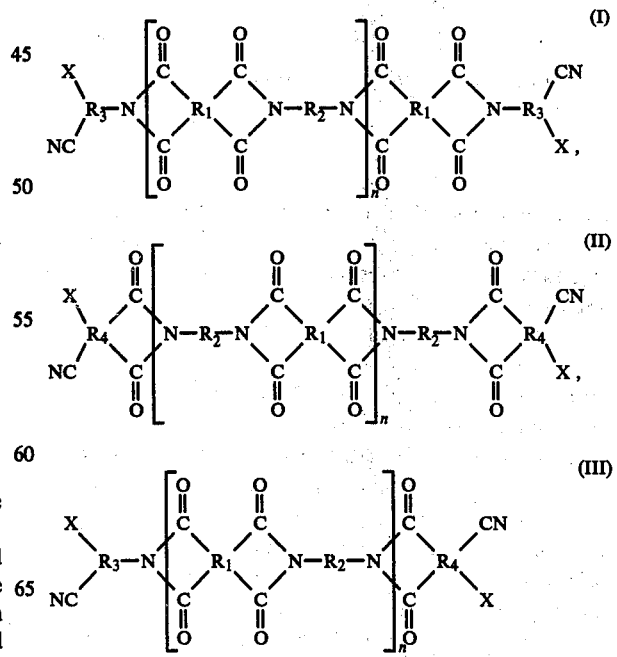

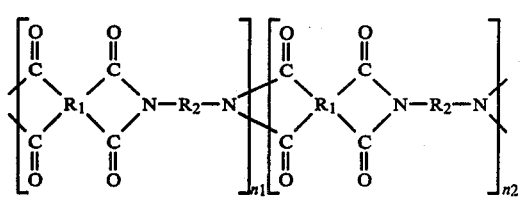
(IV)

which is the reaction product of a tetracarboxylic acid dianhydride (Va), or its derivatives (Vb) having the structural formulas:

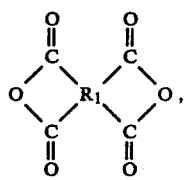
(Va)

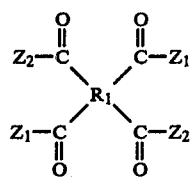
(Vb)

a diamine having the structural formula:

(VI) $H_2N-R_2-NH_2$, with a nitrile having one of the following structural formulas, if prepolymer (I), (II) or (III) is to be made:

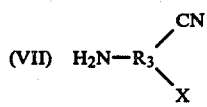
(VII)

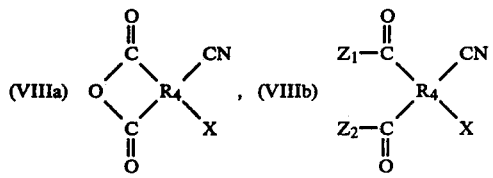
(VIIIa), (VIIIb)

or without a nitrile if prepolymer (IV) is to be made, wherein n is an integer from 0 to 50, depending on the chemical structural formula or the solubility of the aromatic nitrile-modified prepolymer in organic solvents; $n_1$ is either 0 or greater than 1, $n_2$ is a positive integer greater than 1, and the sum of $n_1$ and $n_2$ is an integer from 1 to 50; $R_1$, $R_2$, $R_3$, and $R_4$ are aryl radicals, heterocyclic radicals, particularly those heterocyclic radicals containing one, two, or three nitrogen atoms in the ring, or combination of both aryl and heterocyclic radicals; in prepolymer (IV), $R_1$ and $R_2$ in the brackets followed by the subscript $n_1$ cannot contain a nitrile group, whereas $R_1$ and/or $R_2$ in the brackets followed by the subscript $n_2$ must contain a nitrile group; and in the preferred embodiments $R_1$ is a tetravalent aromatic radical selected from the group consisting of:

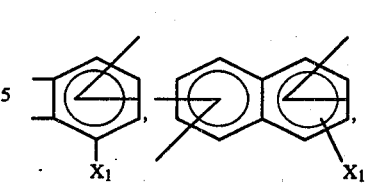

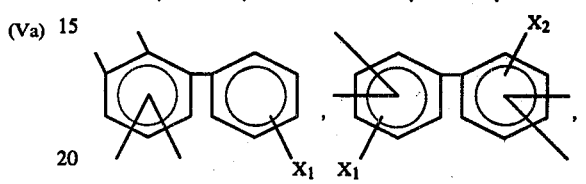

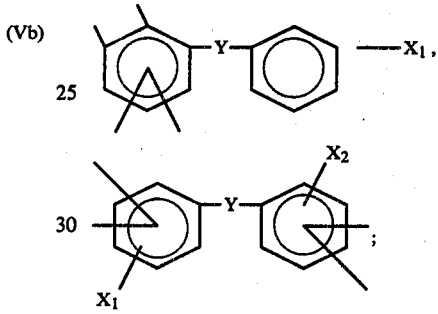

$R_2$ is a bivalent aromatic radical selected from the group consisting of:

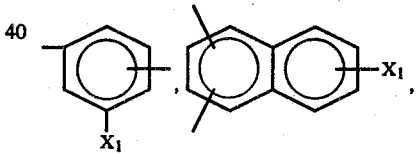

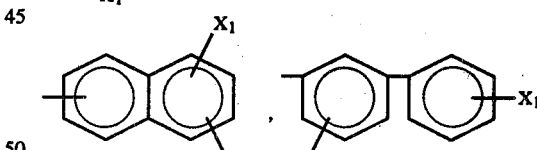

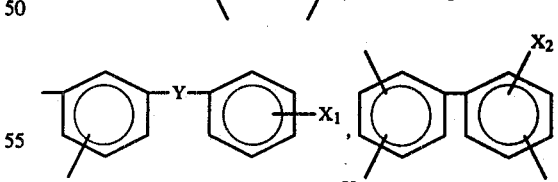

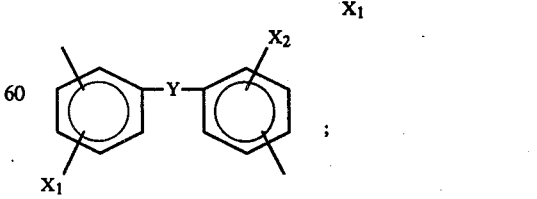

$X_1$ and $X_2$ are monovalent radicals selected from the group consisting of —H, —CN, —F, —Cl, —Br, —NO$_2$, —CH$_3$, and

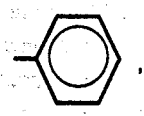

where $X_1$ may or may not be the same group as $X_2$, and X may be either $X_1$ or $X_2$; Y is a bivalent radical selected from the group consisting of:

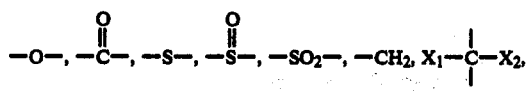

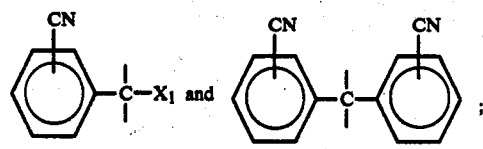

$Z_1$ and $Z_2$ are monovalent radicals selected from the group of: hydroxyl, alkyoxyls, aroxyls, and halides, where $Z_1$ may or may not be the same group as $Z_2$, and Z may be either $Z_1$ or $Z_2$; nitrile (VII) is an aromatic nitrile selected from the group consisting of:

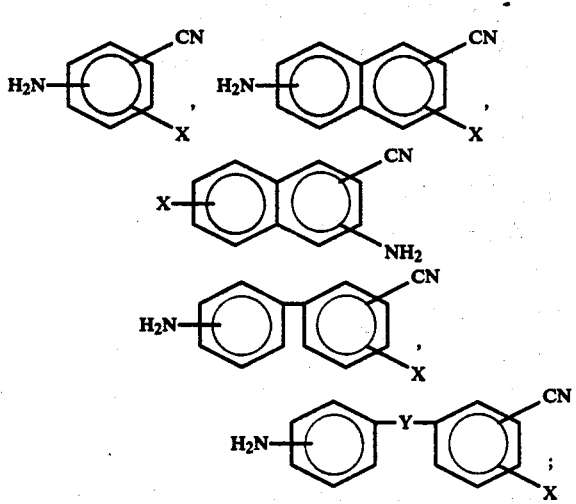

nitrile (VIIIa) is an aromatic nitrile selected from the group consisting of:

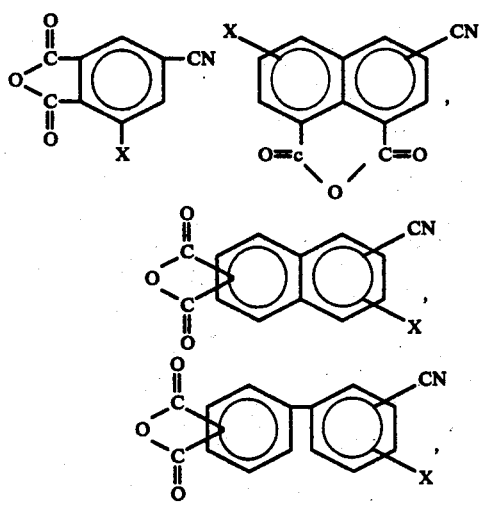

-continued

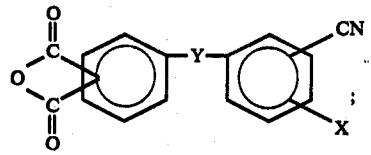

and nitrile (VIIIb) is the derivative of aromatic nitrile (VIIIa), wherein the dicarboxylic acid anhydride moiety becomes either a diacid, a diester, a halfester or a dicarbonyl halide having the two carboxyl or carbonyl groups in the ortho positions on the aryl ring.

The symbol

as used herein indicates that the two ring substituent groups are in ortho positions or neighboring to each other.

It has been found, in accordance with the present invention, that the novel processable aromatic nitrile-modified imide prepolymers disclosed above can be catalytically trimerized using the novel process of the present invention to form high molecular weight aryl-s-triazine ring containing polyimides which exhibit outstanding thermal-oxidative stability and high performance structural properties. These novel aromatic nitrile-modified imide prepolymers are readily processable into filler-reinforced composites by the inclusion of suitable fillers, such as those discussed hereinbefore, in the reaction mixture during the catalytic trimerization process. The novel filler-reinforced composites made from the novel processable aromatic nitrile-modified imide prepolymers may be fabricated into useful articles for industrial and household applications which require a great degree of stability to thermal oxidation as well as excellent mechanical properties at elevated temperatures. The novel filler-reinforced composites of the present invention can be used as structural materials in a number of aeronautical and aerospace applications.

The polybenzimidazole class of polymers find wide utility in numerous areas of application in the form of shaped articles which effectively utilize their highly stable nature. They are particularly useful in the form of films and fibers which show great resistance to degradation by heat, hydrolytic media, and oxidizing media. Fibers of the polymers are of value in numerous textile and industrial uses, and may be woven and knit into fabrics which will retain their properties for extended periods even in uses where other fibers rapidly deteriorate. Films of the polymers are useful in covering and protective agents, even in locations where corrosive conditions prevail. Conventional polybenzimidazoles, however, are difficult to process, with or without filler-reinforcement. According to the present invention, novel aromatic nitrile-modified (terminated and/or appended) benzimidazole prepolymers are produced which may be trimerized to form new triaryl-s-triazine ring crosslinked polybenzimidazoles which possess the outstanding thermal stability of both polybenzimidazoles and triaryl-s-triazines.

The novel processable aromatic nitrile-modified benzimidazole prepolymers made in accordance with the present invention have one of the following four general structural formulas:

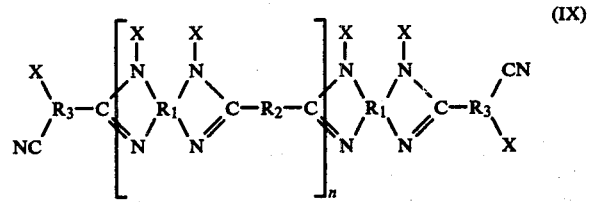 (IX)

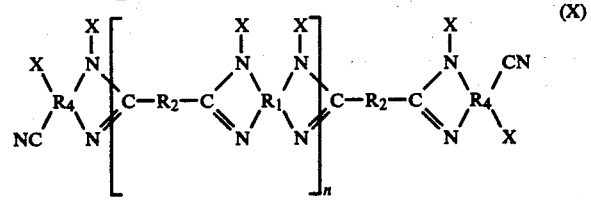 (X)

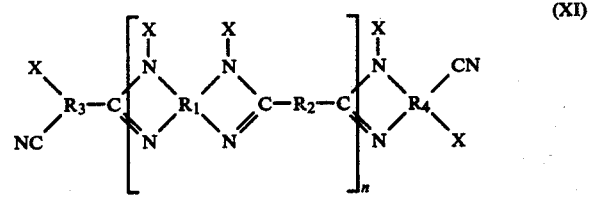 (XI)

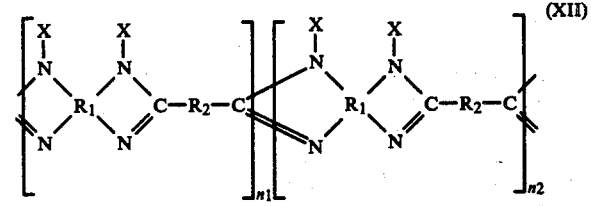 (XII)

which is the reaction product of a dicarboxylic acid or its derivatives having the structural formula:

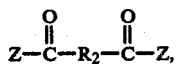 (XIII)

a tetra-amine having the structural formula:

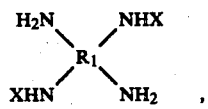 (XIV)

with a nitrile having one of the following structural formulas, if prepolymer (IX), (X) or (XI) is to be made:

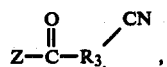 (XV)

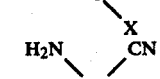 (XVI)

or without a nitrile if prepolymer (XII) is to be made, wherein n is an integer from 0 to 50, depending on the chemical structural formula or the solubility of the aromatic nitrile-modified prepolymer in organic solvents; $n_1$ is either 0 or greater than 1, $n_2$ is a positive integer greater than 1, and the sum of $n_1$ and $n_2$ is a integer from 1 to 50; $R_1$, $R_2$, $R_3$, and $R_4$ are aryl radicals, heterocyclic radicals, particularly those heterocyclic radicals containing one, two, or three nitrogen atoms in the ring, or combination of both aryl and heterocyclic radicals; in prepolymer (XII), $R_1$ and $R_2$ in the brackets followed by the subscript $n_1$ cannot contain a nitrile group, whereas $R_1$ and/or $R_2$ in the brackets followed by the subscript $n_2$ must contain a nitrile group; and in the preferred embodiments $R_1$ is a tetravalent aromatic radical selected from the group consisting of:

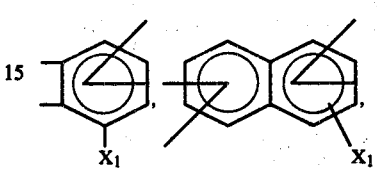

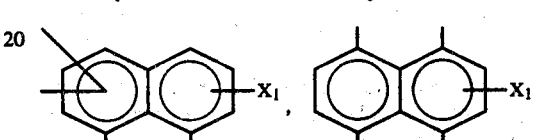

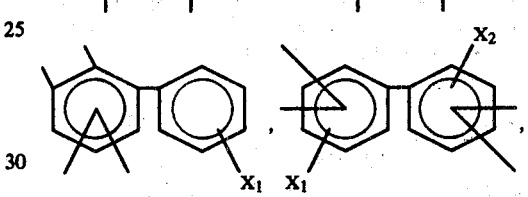

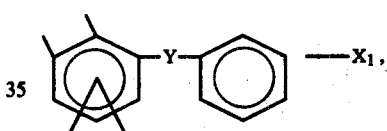

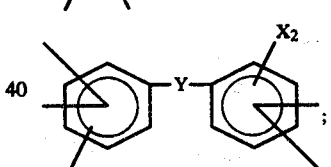
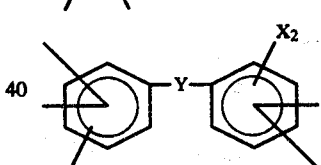

$R_2$ is a bivalent aromatic radical selected from the group consisting of:

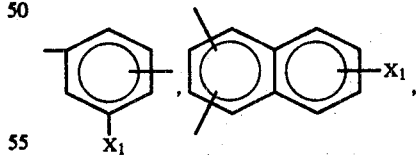

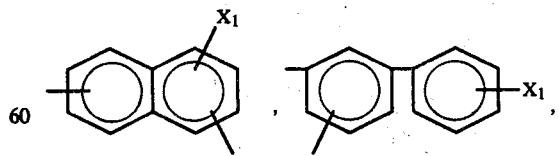

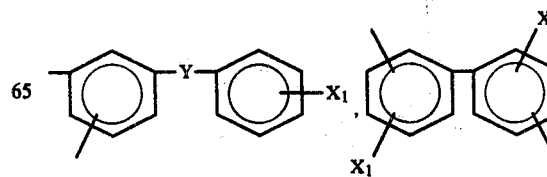
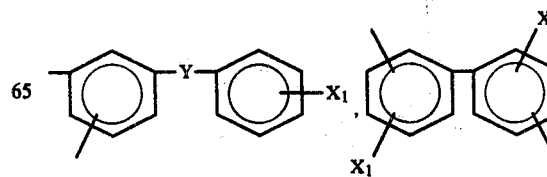

-continued

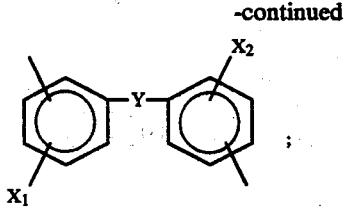

nitrile (XV) is an aromatic nitrile selected from the group consisting of:

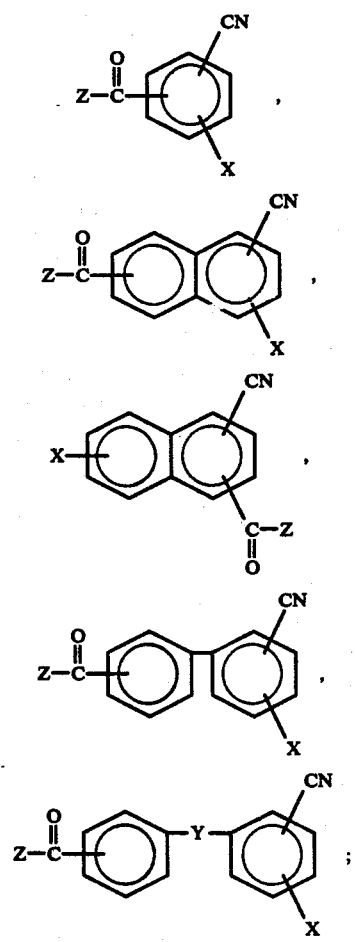

nitrile (XVI) is an aromatic nitrile selected from the group consisting of:

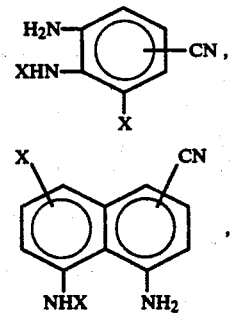

-continued

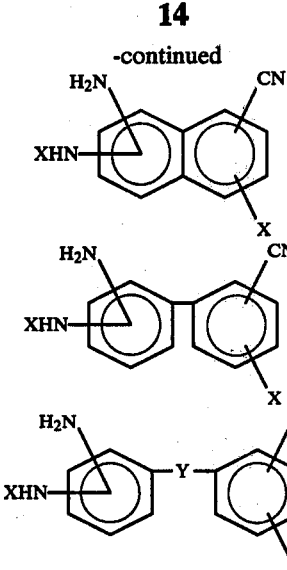

$X_1$ and $X_2$ are monovalent radicals selected from the group consisting of —H, —CN, —F, —Cl, —Br, —$NO_2$, —$CH_3$, and

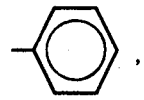

where $X_1$ may or may not be the same group as $X_2$, and X may be either $X_1$ or $X_2$; Y is a bivalent radical selected from the group consisting of:

$$-O-, -\overset{O}{\underset{\|}{C}}-, -S-, -\overset{O}{\underset{\|}{S}}-, -SO_2-, -CH_2, X_1-C-X_2,$$

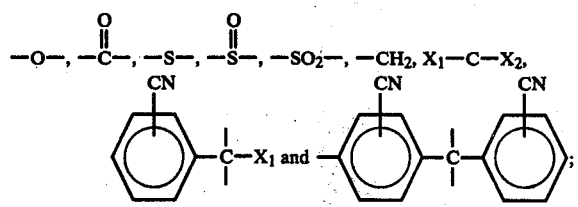

and Z is a monovalent radical selected from the group consisting of: hydroxyl, alkyoxyls, aroxyls, and halides.

It has been found, in accordance with the present invention, that the novel processable aromatic nitrile-modified benzimidaxole prepolymers disclosed above can be catalytically trimerized without the evolution of by-products using the novel process of the present invention to form high molecular weight aryl-s-triazine ring containing polybenzimidazoles.

These novel polybenzimidazole resins find utility as pressure adhesives and composites to form articles which are free of voids and which exhibit good thermal-oxidative stability and high performance structural properties. These novel resins are readily processable into filler-reinforced composites by the inclusion of suitable fillers in the reaction mixture during the catalytic trimerization process as noted above.

The class of polymers known as the polyimidazopyrrolones are known to possess a high resistance to thermal and radiative energy as well as excellent mechanical properties of shaped articles made from the polymers. They also display outstanding resistance to organic chemicals as well as a remarkable resistance to the action of strong acids and bases. Conventional polyimidazopyrrolones, however, are extremely difficult to process, with or without fiber reinforcement. According to the present invention, novel aromatic nitrile-modified (terminated and/or appended) imidazopyrrolone prepolymers are disclosed which may be trimerized to form new triaryl-s-triazine ring containing polyimidazopyrrolones, which possess the good thermal stability of both polyimidazopyrrolones and triaryl-s-triazines.

The novel processable aromatic nitrile-modified imidazopyrrolone prepolymers made in accordance with the present invention have one of the following four general structural formulas:

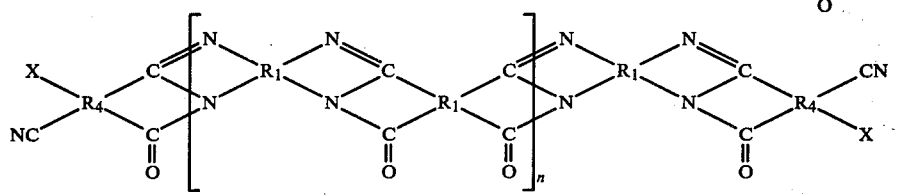

(XVII)

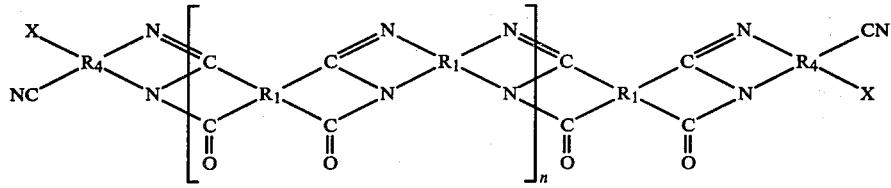

(XVIII)

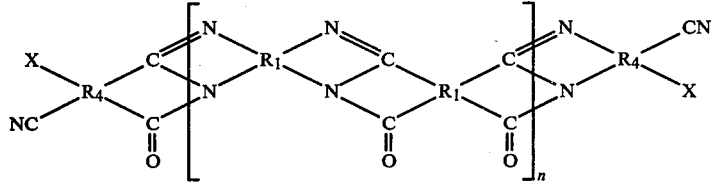

(XIX)

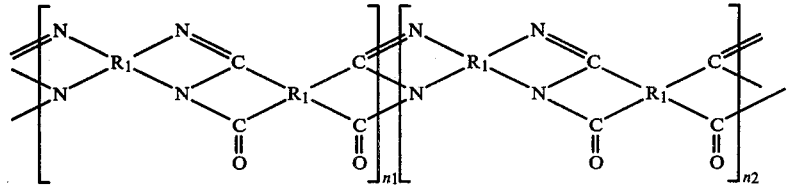

(XX)

which is the reaction product of a tetracarboxylic acid dianhydride (XXIa), or its derivatives (XXIb) having the structural formulas:

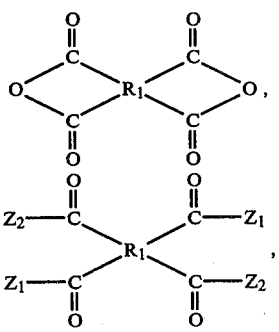

(XXIa)

(XXIb)

a tetra-amine having the structural formula:

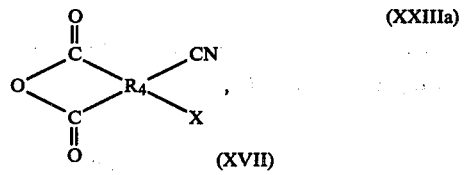

(XXII)

with a nitrile having one of the following structural formulas, if prepolymer (XVII), (XVIII) or (XIX) is to be made:

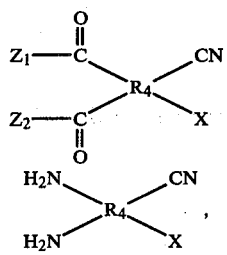

(XXIIIa)

(XXIIIb)

(XXIV)

or without a nitrile if prepolymer (XX) is to be made, wherein n is an integer from 0 to 30, depending on the chemical structural formula or the solubility of the aromatic nitrile-modified prepolymer in organic solvents; $n_1$ is either 0 or greater than 1, $n_2$ is a positive integer greater than 1, and the sum of $n_1$ and $n_2$ is an integer from 1 to 50; $R_1$ and $R_4$ are aryl radicals, heterocyclic radicals, particularly those heterocyclic radicals containing one, two or three nitrogen atoms in the ring, or combination of both aryl and heterocyclic radicals; in prepolymer (XX), $R_1$ in the brackets (followed by the subscript $n_1$ cannot contain a nitrile group, whereas $R_1$ in the brackets followed by the subscript $n_2$ must contain a nitrile group; and in the preferred embodiments $R_1$ is a tetravalent aromatic radical selected from the group consisting of:

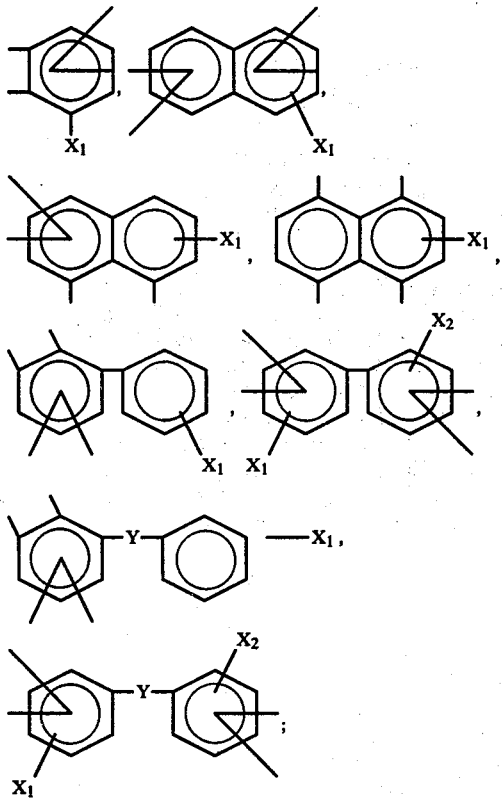

nitrile (XXIIIa) is an aromatic nitrile selected from the group consisting of:

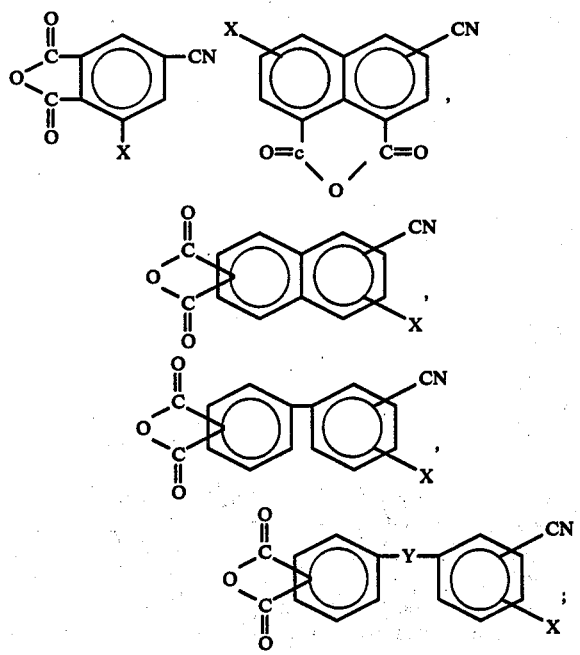

nitrile (XXIIIb) is the derivative of aromatic nitrile (XXIIIa), wherein the dicarboxylic acid anhydride moiety becomes either a diacid, a diester, a halfester or a dicarbonyl halide having the two carboxyl or carbonyl groups in the ortho positions on the aryl ring; nitrile (XXIV) is an aromatic nitrile selected from the group consisting of:

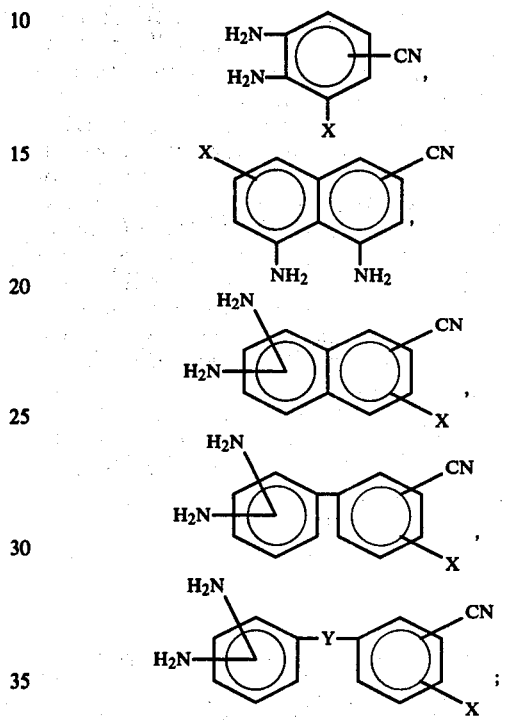

$X_1$ and $X_2$ are monovalent radicals selected from the group consisting of —H, —CN, —F, —Cl, —Br, —$NO_2$, —$CH_3$, and

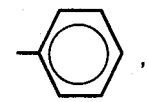

where $X_1$ may or may not be the same group as $X_2$, and X may be either $X_1$ or $X_2$;

Y is a bivalent radical selected from the group consisting of:

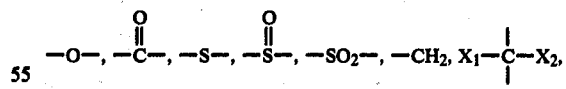

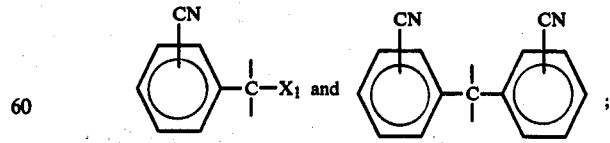

and $Z_1$ and $Z_2$ are monovalent radicals selected from the group consisting of: hydroxyl, alkyoxyls, aroxyls, and halides, where $Z_1$ may or may not be the same group as $Z_2$, and Z may be either $Z_1$ or $Z_2$.

It has been found, in accordance with the present invention that the novel processable aromatic nitrile-modified imidazopyrrolone prepolymers disclosed above can be catalytically trimerized without the evolution of by-products using the novel process of the present invention to form high molecular weight aryl-s-triazine ring containing polyimidazopyrrolones. These novel polyimidazopyrrolone resins also find utility as pressure adhesives and composites to form articles which are free of voids and which exhibit outstanding thermal-oxidative stability and high performance structural properties. These novel resins are readily processable into filler-reinforced composites by the inclusion of suitable fillers in the reaction mixture during the catalytic trimerization process as noted above.

The class of polymers known as the polyquinoxalines are also known to possess a high resistance to thermal energy as well as excellent mechanical properties of shaped articles made from the polymers. Conventional polyquinoxalines, however, are also difficult to process, with or without filler-reinforcement. According to the present invention novel aromatic nitrile-modified quinoxaline prepolymers are disclosed which may be trimerized to form new processable polyquinoxalines which possess the good thermal stability of both polyquinoxalines and triaryl-s-triazines.

The novel processable aromatic nitrile-modified quinoxaline prepolymers made in accordance with the present invention have one of the following four general structure formulas:

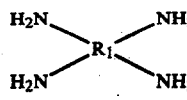

with a nitrile having one of the following structural formulas, if prepolymer (XXV), (XXVI) or (XXVII) is to be made:

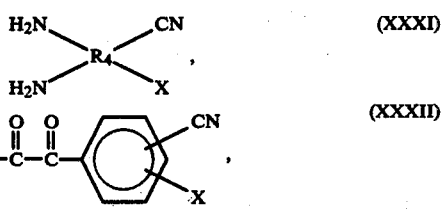

or without a nitrile if prepolymer (XXVIII) is to be made, wherein n is an integer of 0 to 100, depending on the chemical structural formula or the solubility of the aromatic nitrile-modified prepolymer in organic solvents; $n_1$ is either 0 or greater than 1, $n_2$ is a positive integer greater than 1, and the sum of $n_1$ and $n_2$ is an integer from 1 to 100; $R_1$, $R_2$, and $R_4$ are aryl radicals, heterocyclic radicals, particularly those heterocyclic radicals containing one, two, or three nitrogen atoms in the ring, or a combination of both aryl and heterocyclic radicals; in prepolymer (XXVIII), $R_1$ and $R_2$ in the brackets followed by the subscript $n_1$ cannot contain a nitrile group, whereas $R_1$ and/or $R_2$ in the brackets followed by the subscript $n_2$ must contain a nitrile group; and in the preferred embodiments $R_1$ is a tetravalent aromatic radical selected from the group consisting of:

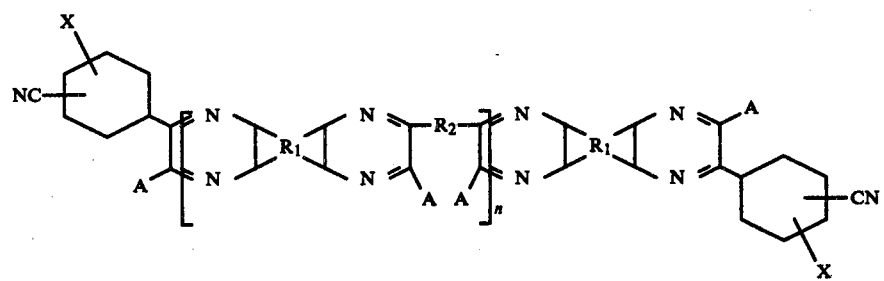

(XXV)

(XXVI)

(XXVII)

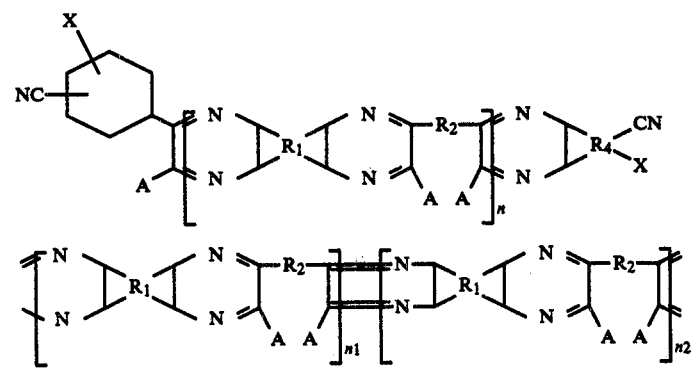

(XXVIII)

which is the reaction product of a diglyoxal having the structural formula:

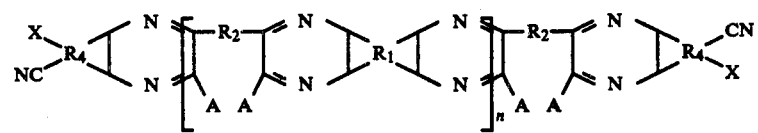

(XXIX)

a tetra-amine having the structural formula:

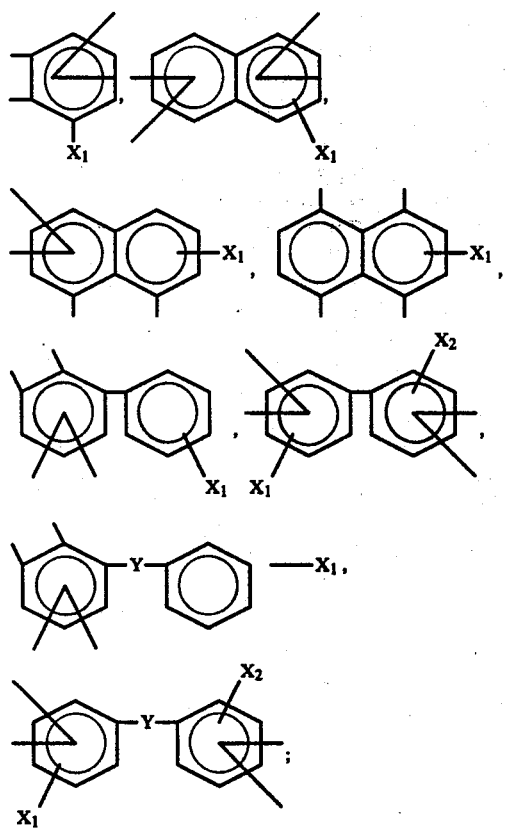

$R_2$ is a bivalent aromatic radical selected from the group consisting of:

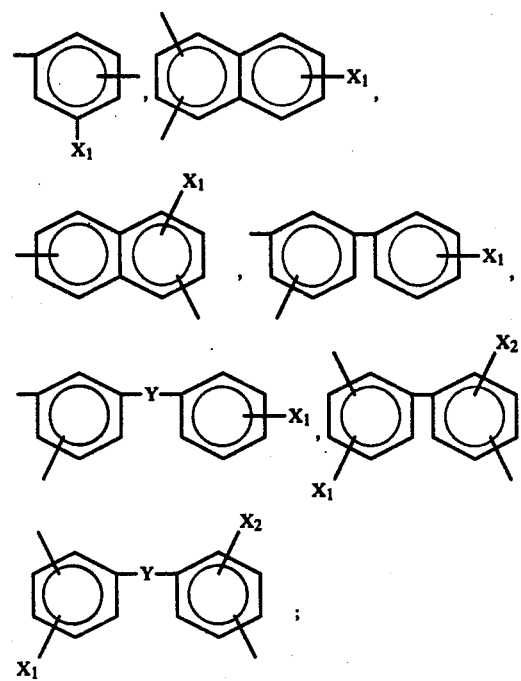

nitrile (XXXI) is an aromatic nitrile selected from the group consisting of:

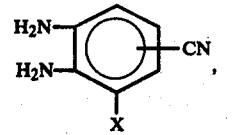

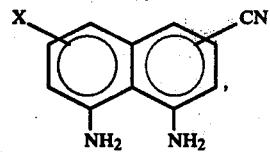

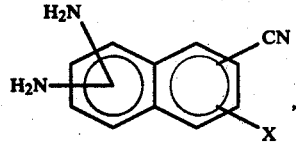

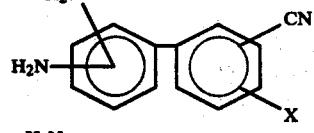

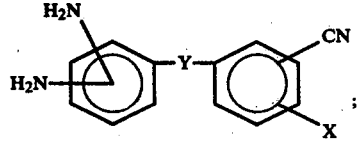

$X_1$ and $X_2$ are monovalent radicals selected from the group consisting of —H, —CN, —F, —Cl, —Br, —NO$_2$, —CH$_3$, and

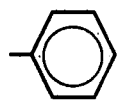

where $X_1$ may or may not be the same group as $X_2$, and X may be either $X_1$ or $X_2$; Y is a bivalent radical selected from the group consisting of:

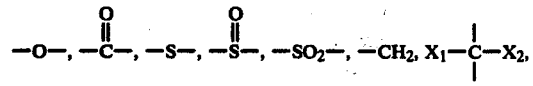

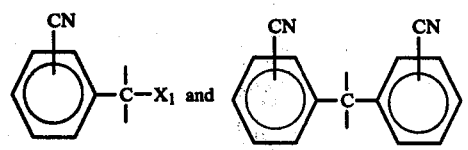

and A is a monovalent radical selected from the group consisting of:

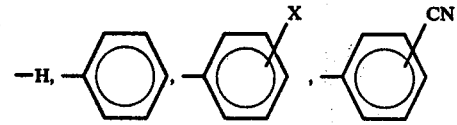

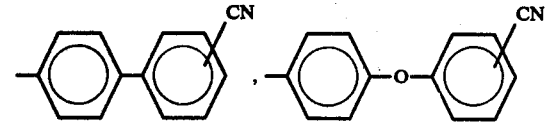

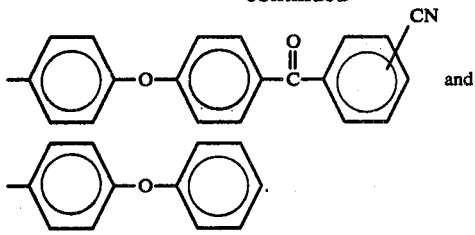

It has been found, in accordance with the present invention, that the novel processable aromatic nitrile-modified quinozaline prepolymers disclosed above can be catalytically trimerized without the evolution of by-products using the novel process of the present invention to form high molecular weight aryl-s-triazine ring containing polyquinoxalines. These novel polyquinoxaline resins also find utility as pressure adhesives and article-forming composites which exhibit good thermal-oxidative stability and high performance structural properties. These novel resins are readily processable into filler-reinforced composites by the inclusion of suitable fillers in the reaction mixture during the catalytic trimerization reaction process as noted above.

As described above, the four classes of polymers known as polyimides, polybenzimidazoles, polyimidazopyrrolones, and polyquinoxalines are known to possess a high resistance to thermal energy as well as excellent mechanical properties of shaped articles made from the polymers with or without filler reinforcement. According to the present invention novel aromatic nitrile-modified (terminated and/or appended) precopolymers made from combinations of the four classes of prepolymers are disclosed which may be trimerized to form novel processable copolymers which possess the good thermal stability of these four classes of polymers and triaryl-s-triazines. The novel precopolymers are made by combining two, three or four of the classes of prepolymers disclosed above.

The novel processable aromatic nitrile-modified precopolymer combinations of imide, benzimidazole, imidazopyrrolone and quinoxaline prepolymers are made by selecting appropriate monomeric reactants set forth in Table II below and appropriate terminating nitrile reagents set forth in Table III below.

TABLE II
HIGH TEMPERATURE RESISTANT POLYMERS

TABLE II-continued
HIGH TEMPERATURE RESISTANT POLYMERS

| Polymer | Monomeric Reactants | | Linkage |
|---|---|---|---|
| | 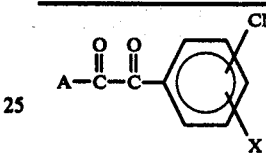 | | |
| Quinoxalines | 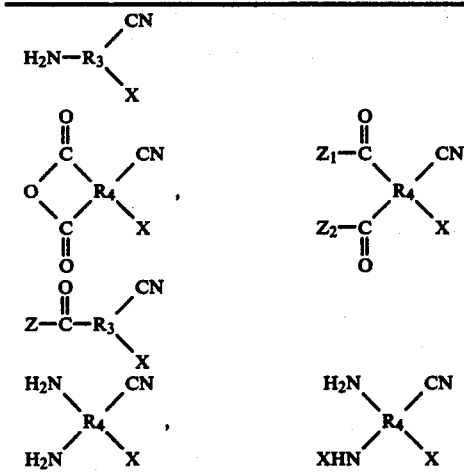 | | |

TABLE III
TERMINATING OR END-CAPPING NITRILE REAGENTS
Nitrile Reagent

TABLE III-continued
TERMINATING OR END-CAPPING NITRILE REAGENTS
Nitrile Reagent As will be readily apparent to those skilled in the art, the novel aromatic nitrile-modified precopolymer combinations can be easily formulated by selecting appropriate monomeric reactants and terminating nitrile reagents from two, three or four of the classes of novel processable aromatic nitrile-modified prepolymers disclosed above.

For example, a novel processable aromatic nitrile-modified imide-imidazopyrrolone precopolymer made in accordance with the present invention can have the structural formula:

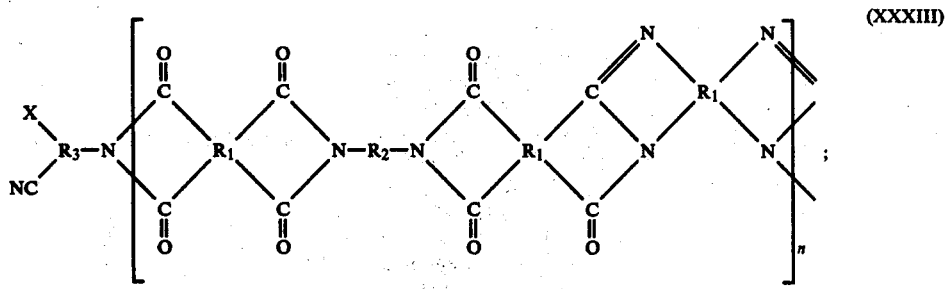

(XXXIII)

a novel processable aromatic nitrile-modified quinoxaline-benzimidazole precopolymer made in accordance with the present invention can have the structural formula:

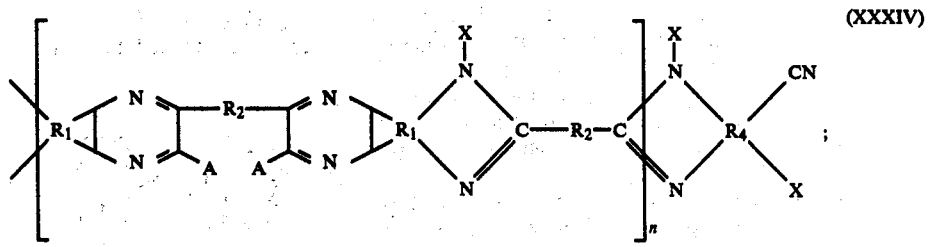

(XXXIV)

a novel processable aromatic nitrile-modified imide-imidazopyrrolone-quinoxaline precopolymer made in accordance with the present invention can have the structural formula:

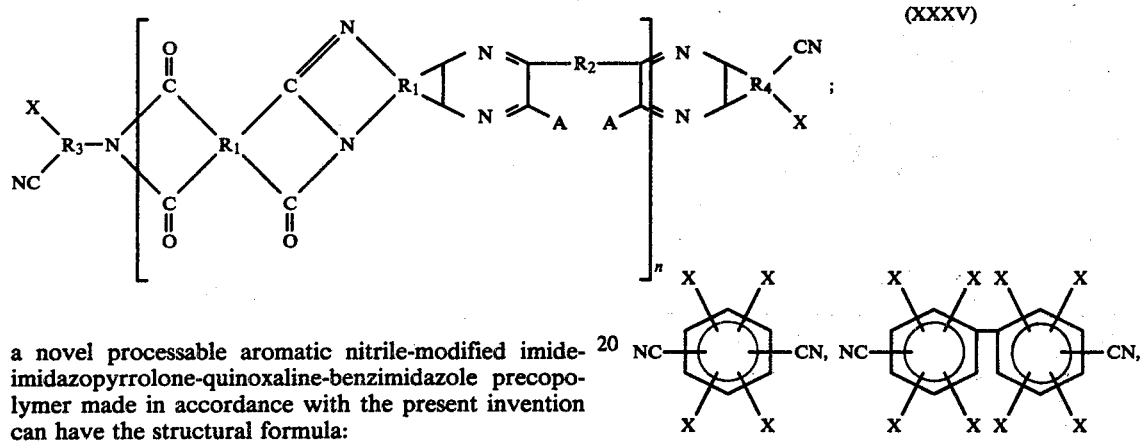

(XXXV)

a novel processable aromatic nitrile-modified imide-imidazopyrrolone-quinoxaline-benzimidazole precopolymer made in accordance with the present invention can have the structural formula:

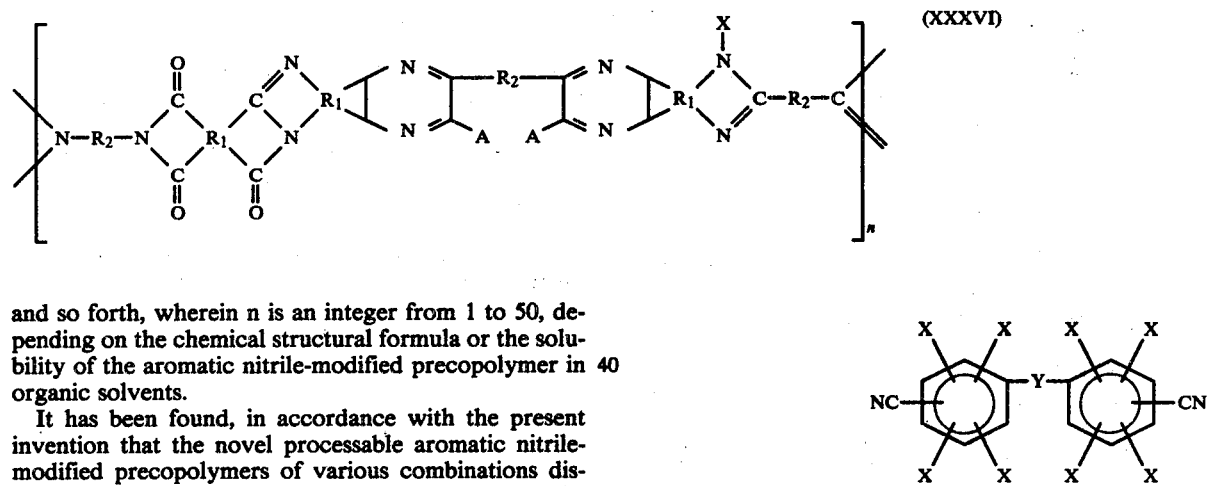

(XXXVI)

and so forth, wherein n is an integer from 1 to 50, depending on the chemical structural formula or the solubility of the aromatic nitrile-modified precopolymer in organic solvents.

It has been found, in accordance with the present invention that the novel processable aromatic nitrile-modified precopolymers of various combinations disclosed above can be catalytically trimerized without the evolution of by-products using the novel process of the present invention to form high molecular weight corresponding triaryl-s-triazine ring cross-linked copolymers. These novel copolymer resins also find utility as pressure adhesives and composites to form articles which are free of voids and which exhibit outstanding thermal-oxidative stability and high performance structural properties. These novel resins are readily processable into filler-reinforced composites by the inclusion of suitable fillers in the reaction mixture during the catalytic trimerization process as noted above.

Further, in accordance with the present invention, it was found that certain aromatic dinitrile compounds including aromatic nitrile end-capped methylene, phenylene, arylether, arylsulfide, arylsulfone, arylketone, siloxane prepolymers and their precopolymers can be catalytically trimerized according to the novel process of the present invention to form novel polymeric products containing triarly-s-triazine rings which exhibit good thermal-oxidative stability.

The processable aromatic dinitrile compounds which may be catalytically trimerized in accordance with the present invention consist of the following:

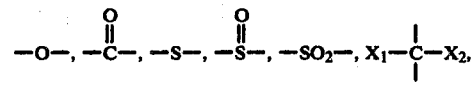

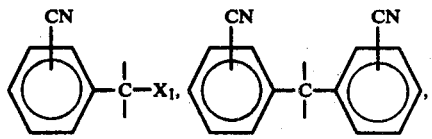

wherein Y is a bivalent radical selected from the group consisting of:

$$-O-, -\overset{O}{\underset{\|}{C}}-, -S-, -\overset{O}{\underset{\|}{S}}-, -SO_2-, X_1-\overset{|}{\underset{|}{C}}-X_2,$$

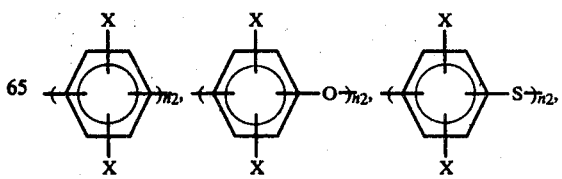

$-(CH_2)_{n1}$, $-(CF_2)_{n1}$, and $-(CH_2\text{-}CFCl)_{n1}$, where $n_1$ is an integer from 1 to 4, and -continued

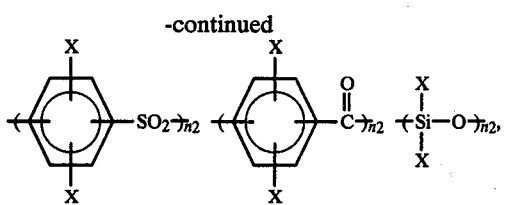

and combinations thereof, where $n_2$ is an integer from 1 to about 100; and X is a monovalent radical selected from the group consisting of —H, —F, —Cl, —Br, —NO$_2$, —CH$_3$, and

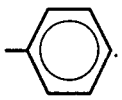

These novel polymeric products containing triaryl-s-triazine rings also find utility in filler-reinforced composites of high thermal-oxidative stability and high performance structural properties which are useful as structural materials in a number of aeronautical and aerospace applications.

A more complete appreciation of the invention will be realized by reference to the following specific examples relating to specific compounds and polymers and the processes for preparing them. The following examples are not intended to limit the invention disclosed herein except to the extent that limitations are specifically stated or to the extent to which limitations appear in the appended claims.

EXAMPLE 1

Benzonitrile in the amount of 0.01 mole was mixed with 5 mole percent of p-toluenesulfonic acid monohydrate and introduced into a 45 milliliter stainless steel pressure vessel equipped with a 1000 p.s.i. pressure gauge, a 1000 p.s.i. burst disc and a needle valve. The pressure was then brought up to 600 p.s.i. by introducing compressed nitrogen into the vessel and the temperature was raised to 232° C. for a period of 48 hours. The product was then separated from the unreacted nitrile and the catalyst and recrystallized from a suitable solvent. The product obtained was analyzed by infrared and its melting point was determined to be 232°-235° C. The percent yield, i.e percent of converted nitrile which is triazine, was found to be 14 percent.

EXAMPLE 2

Using the apparatus described in Example 1, 0.01 mole of cyanobenzoic acid was mixed with 5 mole percent of p-toluenesulfonic acid monohydrate. The mixture was heated at 232° C. and 750 p.s.i. for 48 hours. The product was then separated from the unreacted nitrile and the catalyst and recrystallized from glacialacetic acid. The product was analyzed by infrared and its melting point was determined to be >340° C. The percentage of yield was found to be 75 percent.

EXAMPLE 3 p-Cyanophthalanil, [N-(4-Cyanophenyl)phthalimide], was prepared from p-aminobenzonitrile and phthalic anhyrdide. p-Cyanophthalanil is a white crystalline powder having a melting point of 189° C. (lit. 187° C.). Its infrared spectrum showed a nitrile band at 2240 cm$^{-1}$, imide bands at 1795, 1775, 1735, and 1380 cm$^{-1}$, and aromatic ring bands at 1610 and 1520 cm$^{-1}$ respectfully. Catalytic trimerization of 0.01 mole of p-cyanophthalanil with 5 mole percent of p-toluenesulfonic acid monohydrate using the apparatus described in Example 1 at 250° to 300° C. and 720 to 800 p.s.i. for 90 hours gave a product (97 percent yield), m.p. >340° C. The infrared spectrum of the trimerized product showed that the band at 2240 cm$^{-1}$ had disappeared and the bands at 1520 and 1380 cm$^{-1}$ broadened indicating the formation of s-triazine rings.

EXAMPLE 4

Using the apparatus described in Example 1, 0.01 mole of terephthalonitrile, m.p. 231° C., was heated with 5 mole percent of p-toluenesulfonic acid monohydrate at 232° C. and 750 p.s.i. for 48 hours gave a product (99.5% yield), m.p. >340° C. The infrared spectrum of terephthalonitrile showed a very strong nitrile band at 2230 cm$^{-1}$ and a sharp aromatic ring band at 1500 cm$^{-1}$, while the infrared spectrum of the trimerized polymeric product showed strong and broad characteristic s-triazine ring bands at 1525 and 1370 cm$^{-1}$ with a residual nitrile band of medium strength at 2230 cm$^{-1}$. Thermal gravimetric analysis showed that the weight losses of the triaryl-s-triazine ring cross-linked polymeric product were about 7 percent after heating to 316° C. and 18 percent after heating to 538° C.

EXAMPLE 5

In a 100 milliliter glass flask, 9.27 grams (0.00302 mole) of 3,3',4,4'-benzophenonetetracarboxylic dianhydride was heated with 29 grams of anhydrous methanol until a clear solution was obtained. After cooling, 4.02 grams (0.00202 mole) of 4,4'-methylenedianiline, 2.36 grams (0.00200 mole) of p-aminobenzonitrile, and about 0.1 gram (about 0.25 mole percent on basis of the nitrile content) of p-toluenesulfonic acid monohydrate were introduced with stirring until all was dissolved. This clear solution of monomeric reactants was transferred to the apparatus described in Example 1, except that the lid was not installed at this time. The open vessel was heated gradually to about 100° C. so that most of the methanol and some of the by-products (methanol and water) would evaporate off. The reaction vessel was then installed with the lid and heated under reduced pressure at a temperature up to about 200° C. until no more methanol and/or water came off. The vessel was then filled with dry nitrogen gas and adjusted to a pressure in the range of 400 to 800 p.s.i. and heated at temperatures in the range of 200° to 350° C. for 8 hours. The polymeric product presumed to be triaryl-s-triazine ring cross-linked polyimide was found to be very hard and dark brown in color. It did not melt when heated up to 340° C.

EXAMPLE 6

The clear solution of monomeric reactants prepared according to the method described in Example 5 was used to make prepregs by drum winding and impregnating Hercules HMS graphite fiber in a resin/fiber content of about 40/60 by weight. The prepregs were heated from 50° to 120° C. for a couple of hours to reduce the solent content to less than 10 percent by weight. Plys of partially imidized prepregs were then stacked between aluminum foil and heated in an oven at 200° to 250° C. for several hours for complete imidization. The imidized prepregs were then placed in a mold and trimerized at 200° to 350° C. and under pressures in the range of 200 to about 1000 p.s.i. for several hours. The prepregs may be further post cured in an oven at about 300° to 350° C. from several hours to several days.

EXAMPLE 7

Using the apparatus and procedure of Example 5, a triaryl-s-triazine ring containing polybenzimidazole is prepared by reacting 22.50 grams of a solvent mixture of methanol and N-methylpyrrolidone, 3.22 grams of methyl-p-cyanobenzoate, 5.99 grams of dimethyl-terephthalate, 9.88 grams of 3,3',4,4'-tetraminobenzophenone, and 0.10 grams of benzenesulfonic acid.

EXAMPLE 8

Using the apparatus and procedures of Example 5, a triaryl-s-triazine ring cross-linked polybenzimidazole is prepared by reacting 22.50 grams of a solvent mixture of methanol and N-methylpyrrolidone, 1.33 grams of 3,4-diaminobenzonitrile, 9.65 grams of dimethyl-5-cyanoisophthalate, 8.23 grams of 3,3',4,4'-tetraminobenzophenone, and 0.15 grams of naphthalene β-sulfonic acid monohydrate.

EXAMPLE 9

Using the apparatus and procedure of Example 5, a triaryl-s-triazine ring cross-linked benzimidazole-imidazopyrrolone copolymer is prepared by reacting 22.50 grams of a solvent mixture of dimethylsulfoxide and N-methylpyrrolidone, 3.46 grams of 4-cyanophthalic anhydride, 6.42 grams of dimethyl-5-cyanoisophthalate, 9.51 grams of 3,3',4,4'-tetraminobenzophenone, and 0.10 grams of benzenephosphenic acid.

EXAMPLE 10

Using the apparatus and procedure of Example 5, a triazine ring containing polyimidazopyrrolone is prepared by reacting 5.00 grams of methanol, 15.00 grams of N,N-dimethyl formamide, 6.44 grams of 3,3',4,4'-tetramiobenzophenone, 2.66 grams of 3,4-diaminobenzonitrile, and 0.10 grams of ferric acetylacetonate.

EXAMPLE 11

Using the apparatus and procedure similar to Example 5, a triazine ring containing polyimidazopyrrolone is prepared by reacting 8.76 grams of dimethyl-4-cyanophthalate, 4.84 grams of 3,3',4,4'-tetraminobenzophenone, 10 grams of N-methylpyrrolidone, 10 grams of dimethylsulfoxide, and 0.15 grams of 2,6-naphthalene-disulfonic acid.

EXAMPLE 12

Using the apparatus and procedure similar to Example 5, a triaryl-s-triazine ring cross-linked polyimidazopyrrolone is prepared by reacting 8.76 grams of dimethyl-4-cyanophthalate, 5.32 grams of 3,4-diaminobenzonitrile, 10 grams of N,N-dimethylformamide, 10 grams of N,N-dimethylacetamide, 0.05 grams of p-toluenesulfonic acid, and 0.05 grams of zinc acetylacetonate.

EXAMPLE 13

Using the apparatus and procedure similar to Example 5, a triaryl-s-triazine ring cross-linked polyimide is prepared by reacting 2.01 grams of 4,4'-methylenedianiline, 1.33 grams of 3,5-diaminobenzonitrile, 9.27 grams of 3,3',4,4'-benzophenonetetracarboxylic dianhydride, 15 grams of methanol, 15 grams of N-methylpyrrolidone, and about 0.05 grams of p-toluenesulfonic acid monohydrate and 0.05 grams of 3-nitrophenylphosphonic acid.

EXAMPLE 14

Using the apparatus and procedure similar to Example 5, a triazine ring containing polyquinoxaline is prepared by reacting 20.00 grams of N-methylpyrrolidone, 4.70 grams of p-cyanophenyl-glyoxyloylbenzene, 10.2 grams of 1,4-bis(phenylglyoxaloyl) benzene, 9.68 grams of 3,3',4,4'-tetraminobenzophenone, and 0.10 gram of p-toluenesulfonic acid monohydrate.

EXAMPLE 15

Using the apparatus and procedure similar to Example 5, a triazine ring containing quinoxaline-imidazopyrrolone copolymer is prepared by reacting 30.00 grams of N,N-methylpyrrolidone, 3.46 grams of 4-cyanophthalic anhydride, 9.92 grams of 1,4-bis(phenylglyoxaloyl) benzene, 9.44 grams of 3,3',4,4'-tetraminobenzophenone, and 0.10 gram of 2,4,6-trimethylphosphinic acid.

EXAMPLE 16

Using the apparatus and procedure similar to Example 5, a triazine ring containing polyquinoxaline is prepared by reacting 30.00 grams of N,N-methylpyrrolidone, 2.66 grams of 3,4-diaminobenzonitrile, 13.22 grams of 1,4-bis(phenylglyoxaloyl) benzene, 6.92 grams of 3,3',4,4'-tetraminobenzophenone, and 0.10 gram of zinc acetylacetonate.

EXAMPLE 17

Using the apparatus and procedure similar to Example 5, a triazine ring cross-linked polyquinoxaline is prepared by reacting 4.88 grams of p,p'-oxybis (p''-cyanobenzil), 2.42 grams of 3,3',4,4'-tetraaminobenzophenone, 0.05 grams of naphthalene-β-sulfonic acid monohydrate, 0.01 gram of p-toluenesulfonic acid monohydrate, in a mixture of 10 grams of xylene and 70 grams of m-cresol.

EXAMPLE 18

Using the apparatus and procedure similar to Example 5, a triazine ring cross-linked polyquinoxaline is prepared by reacting 7.84 grams (meta- or para-) bis (p'-cyanobenzoylphenoxyphenylglyoxaloyl) benzene

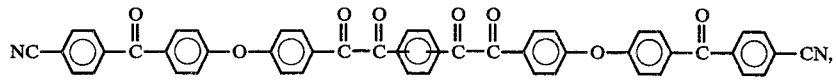

2.42 grams of 3,3',4,4'-tetraaminobenzophenone, 0.05 gram of p-toluenesulfonic acid monohydrate and 0.01 gram of ferric acetylacetonate, in 50 grams of m-cresol and 50 grams of xylene.

What is claimed is:

1. A process for preparing an aromatic 1,3,5-triazine compound from an aromatic nitrile compound which comprises heating the aromatic nitrile compound to a temperature in the range of from about 100° C. to about 700° C. in the presence of a catalyst or mixture of catalysts selected from one or more of the following groups:
(A) organic sulfonic and sulfinic acids,
(B) organic phosphonic and phosphinic acids, and (C) metallic acetylacetonates, at a pressure in the range of from about atmospheric pressures to about 10,000 p.s.i., said process being conducted in the presence of reinforcing filler material.

2. An aromatic nitrile-modified (terminated and/or appended) imide prepolymer having one of the following four general structural formulas:

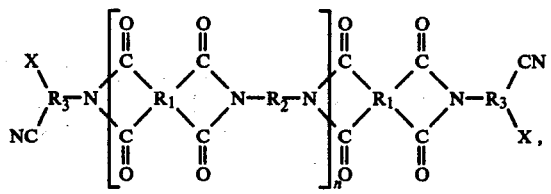

(I)

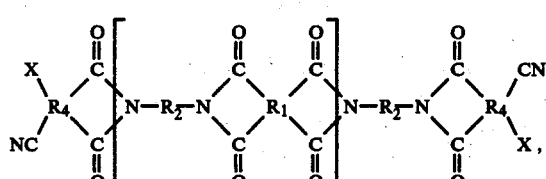

(II)

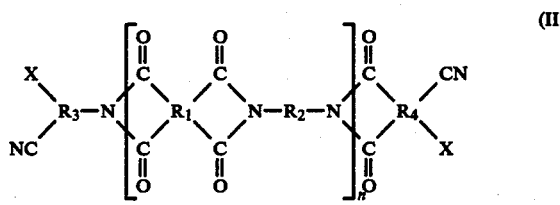

(III)

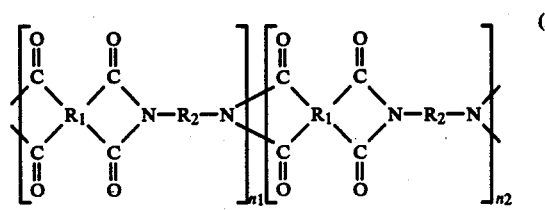

(IV)

which is the reaction product of a tetracarboxylic acid dianhydride (Va), or its derivatives (Vb) having the structural formulas:

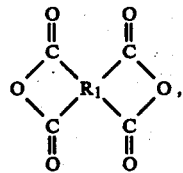

(Va)

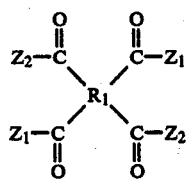

(Vb)

a diamine having the structural formula:

(VI)  $H_2N-R_2-NH_2$, with a nitrile having one of the following structural formulas, if prepolymer (I), (II) or (III) is to be made:

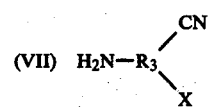

(VII)

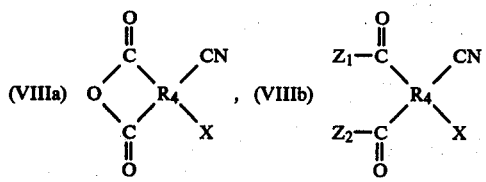

(VIIIa), (VIIIb)

or without a nitrile if prepolymer (IV) is to be made, wherein n is an integer from 0 to 50, depending on the chemical structural formula or the solubility of the aromatic nitrile-modified prepolymer in organic solvents; $n_1$ is either 0 or greater than 1, $n_2$ is a positive integer greater than 1, and the sum of $n_1$ and $n_2$ is an integer from 1 to 50;

$R_1$, $R_2$, $R_3$, and $R_4$ are aryl radicals, heterocyclic radicals, particularly those heterocyclic radicals containing one, two, or three nitrogen atoms in the ring, or combination of both aryl and heterocyclic radicals; in prepolymer (IV), $R_1$ and $R_2$ in the brackets followed by the subscript $n_1$ cannot contain a nitrile group, whereas $R_1$ and/or $R_2$ in the brackets followed by the subscript $n_2$ must contain a nitrile group; and in the preferred embodiments $R_1$ is a tetravalent aromatic radical selected from the group consisting of:

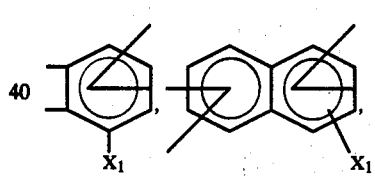

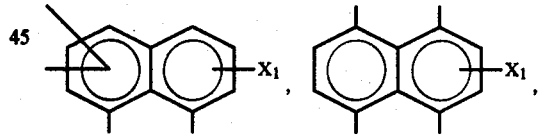

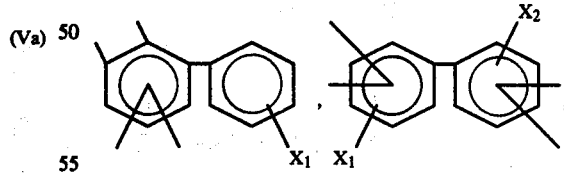

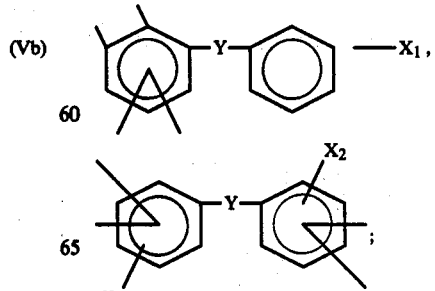

$R_2$ is a bivalent aromatic radical selected from the group consisting of:

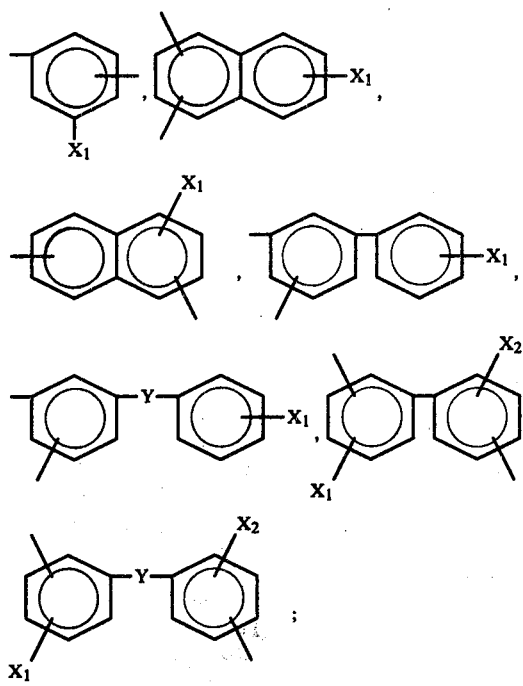

nitrile (VII) is an aromatic nitrile selected from the group consisting of:

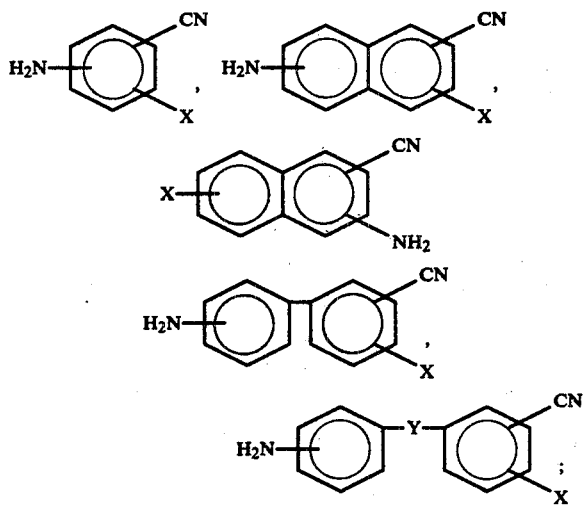

nitrile (VIIIa) is an aromatic nitrile selected from the group consisting of:

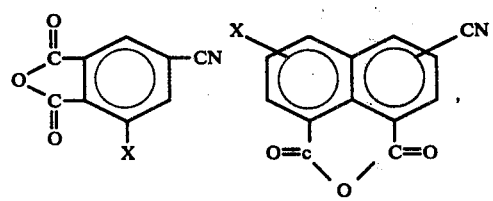

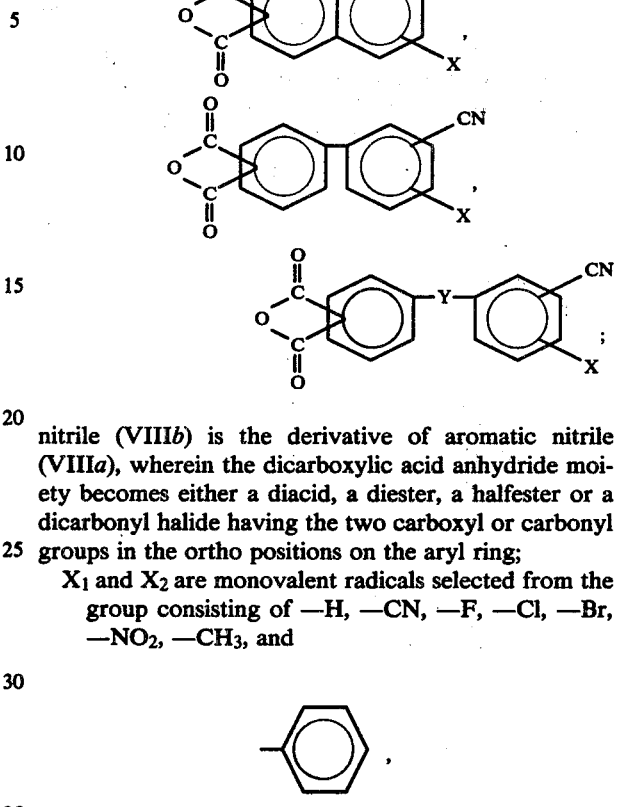

nitrile (VIIIb) is the derivative of aromatic nitrile (VIIIa), wherein the dicarboxylic acid anhydride moiety becomes either a diacid, a diester, a halfester or a dicarbonyl halide having the two carboxyl or carbonyl groups in the ortho positions on the aryl ring;

$X_1$ and $X_2$ are monovalent radicals selected from the group consisting of —H, —CN, —F, —Cl, —Br, —NO₂, —CH₃, and

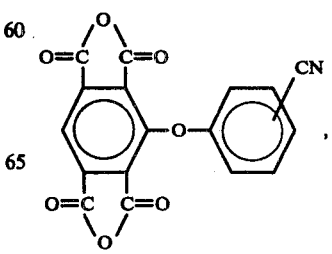

where $X_1$ may or may not be the same group as $X_2$, and X may be either $X_1$ or $X_2$; Y is a bivalent radical selected from the group consisting of:

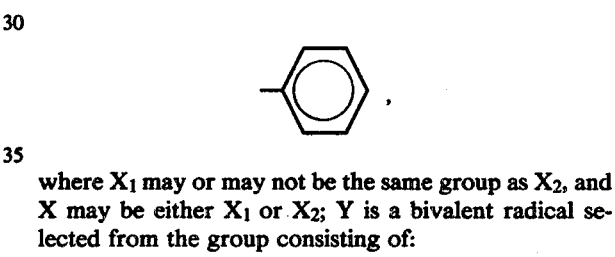

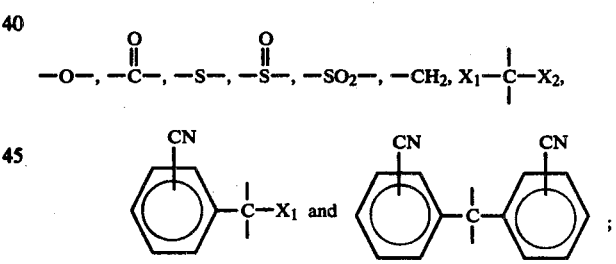

and $Z_1$ and $Z_2$ are monovalent radicals selected from the group of: hydroxyl, alkyoxyls, aroxyls, and halides, where $Z_1$ may or may not be the same group as $Z_2$, and Z may be either $Z_1$ or $Z_2$.

3. An imide prepolymer of claim 2 wherein the tetracarboxylic acid dianhydride (Va), or its derivatives (Vb) are selected from the group consisting of:

-continued

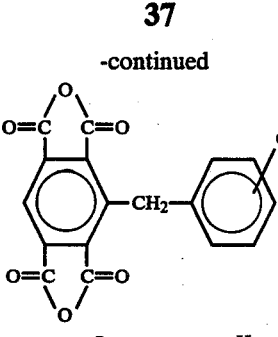

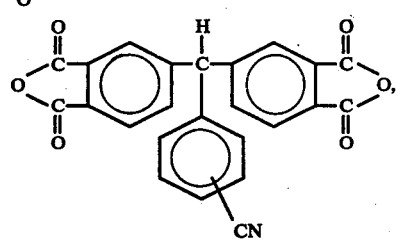

4. An imide prepolymer of claim 2 wherein the diamine (VI) is selected from the group consisting of:

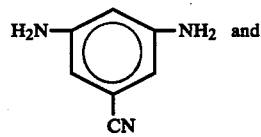

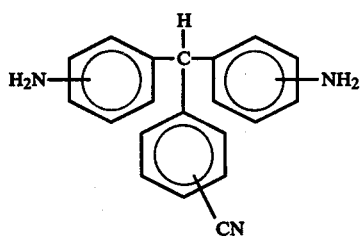

5. A triazine ring containing or cross-linked polymer composition made by catalytically trimerizing an aromatic nitrile-modified imide prepolymer of claim 2.

6. The polymer composition of claim 5 which is catalytically trimerized in the presence of reinforcing filler material.

7. An aromatic nitrile-modified (terminated and/or appended) benzimidazole prepolymer having one of the following four general structural formulas:

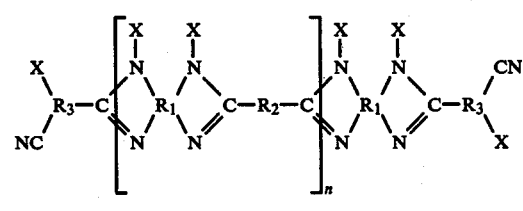

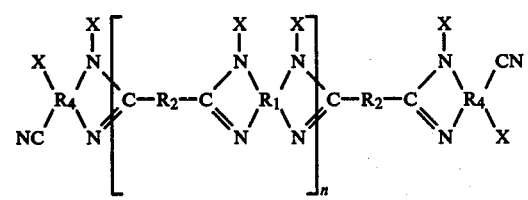

-continued

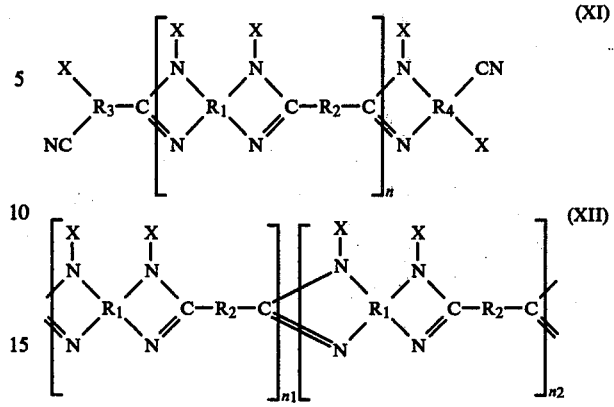

which is the reaction product of a dicarboxylic acid or its derivatives having the structural formula:

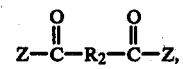

a tetra-amine having the structural formula:

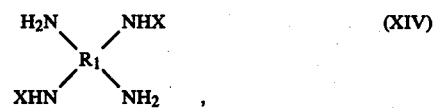

with a nitrile having one of the following structural formulas, if prepolymer (IX), (X) or (XI) is to be made:

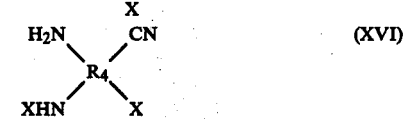

or without a nitrile if prepolymer (XII) is to be made, wherein n is an integer from 0 to 50, depending on the chemical structural formula or the solubility of the aromatic nitrile-modified prepolymer in organic solvents; $n_1$ is either 0 or greater than 1, $n_2$ is a positive integer greater than 1, and the sum of $n_1$ and $n_2$ is an integer from 1 to 50;

$R_1$, $R_2$, $R_3$, and $R_4$ are aryl radicals, heterocyclic radicals, particularly those heterocyclic radicals containing one, two, or three nitrogen atoms in the ring, or combination of both aryl and heterocyclic radicals; in prepolymer (XII), $R_1$ and $R_2$ in the brackets followed by the subscript $n_1$ cannot contain a nitrile group, whereas $R_1$ and/or $R_2$ in the brackets followed by the subscript $n_2$ must contain a nitrile group; and in the preferred embodiments $R_1$ is a tetravalent aromatic radical selected from the group consisting of:

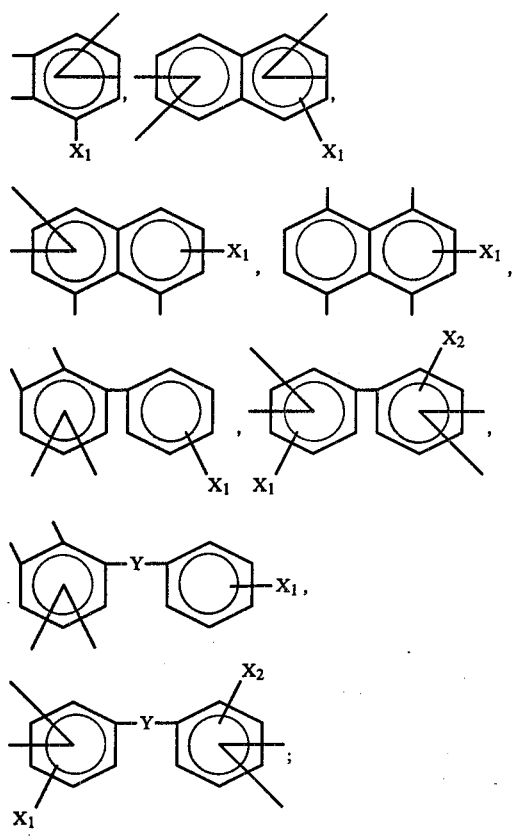
$R_2$ is a bivalent aromatic radical selected from the group consisting of:
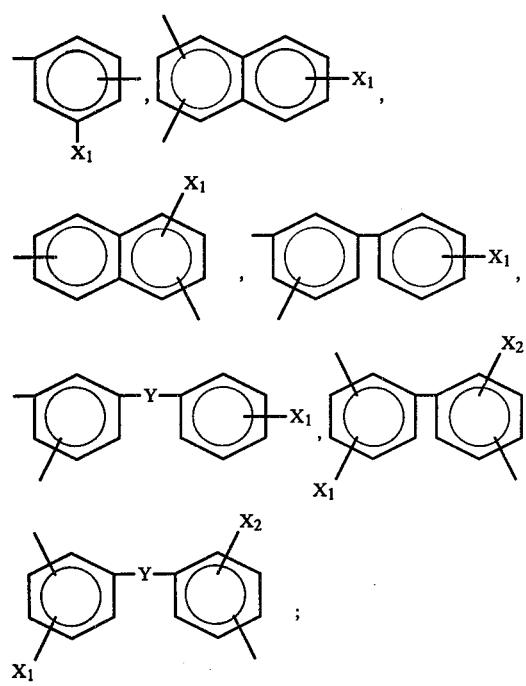
nitrile (XV) is an aromatic nitrile selected from the group consisting of:
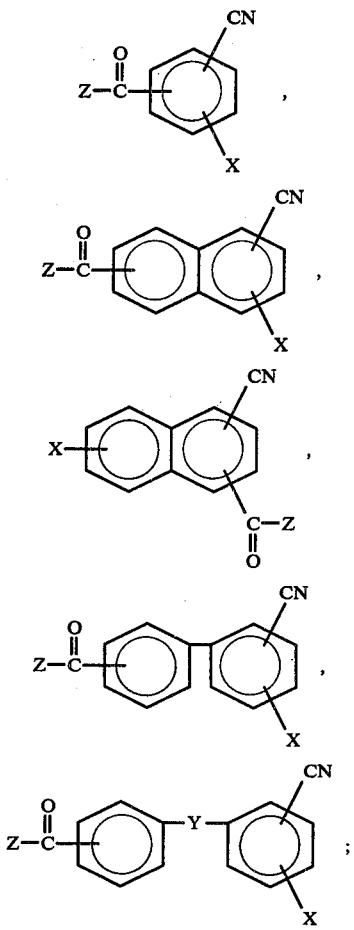
nitrile (XVI) is an aromatic nitrile selected from the group consisting of:
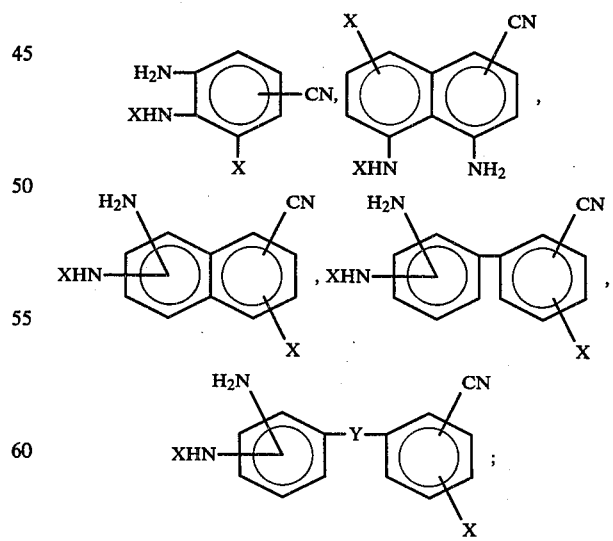
$X_1$ and $X_2$ are monovalent radicals selected from the group consisting of —H, —CN, —F, —Cl, —Br, —NO$_2$, —CH$_3$, and

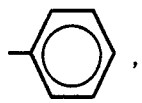

where $X_1$ may or may not be the same group as $X_2$, and X may be either $X_1$ or $X_2$;
Y is a bivalent radical selected from the group consisting of:

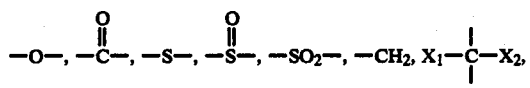

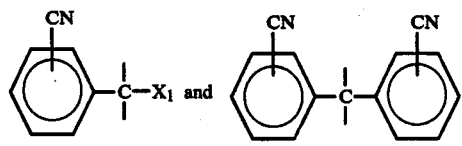

and Z is a monovalent radical selected from the group consisting of:
hydroxyl, alkyoxyls, aroxyls, and halides.

8. A benzimidazole prepolymer of claim 7 wherein the dicarboxylic acid or its derivatives (XIII) is selected from the group consisting of:

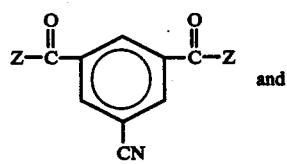

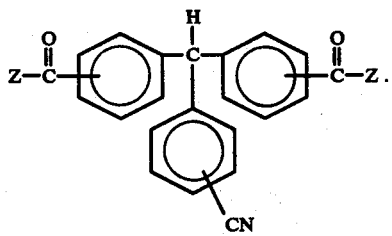

9. A benzimidazole prepolymer of claim 7 wherein the tetra-amine (XIV) is selected from the group consisting of:

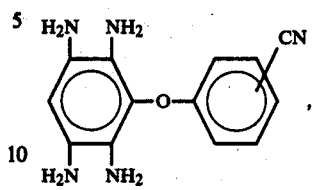

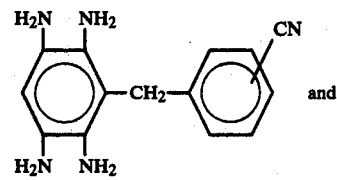

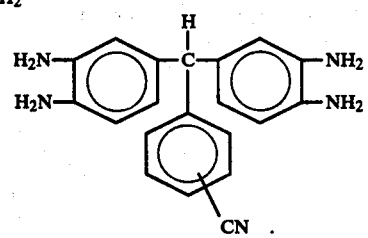

10. A triazine ring containing or cross-linked polymer composition made by catalytically trimerizing an aromatic nitrile-modified benzimidazole prepolymer of claim 7.

11. The polymer composition of claim 10 which is catalytically trimerized in the presence of reinforcing filler material.

12. An aromatic nitrile-modified (terminated and/or appended) imidazopyrrolone prepolymer having one of the following four general structural formulas:

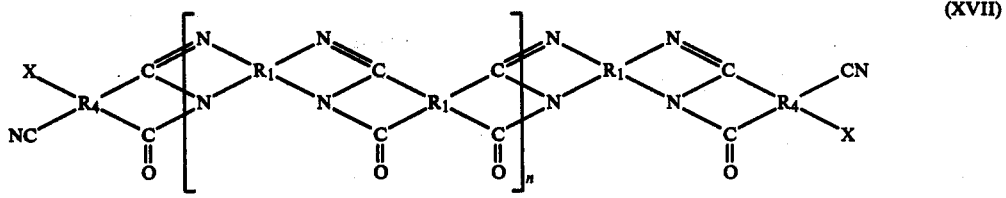

(XVII)

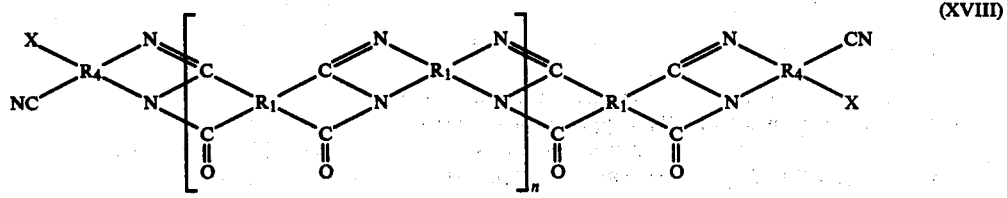

(XVIII)

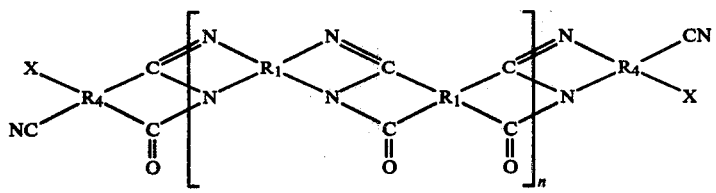 (XIX)

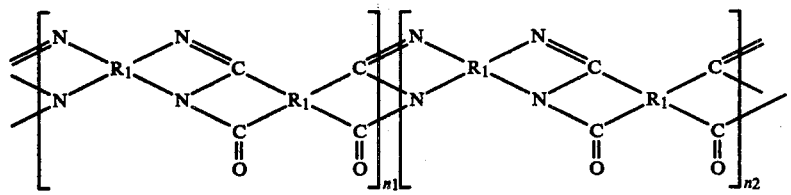 (XX)

which is the reaction product of a tetracarboxylic acid dianhydride (XXIa), or its derivatives (XXIb) having the structural formulas:

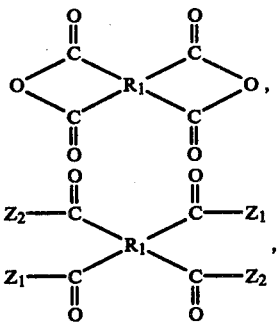 (XXIa)

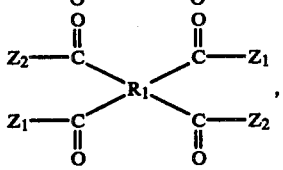 (XXIb)

a tetra-amine having the structural formula:

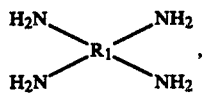 (XXII)

with a nitrile having one of the following structural formulas, if prepolymer (XVII), (XVIII) or (XIX) is to be made:

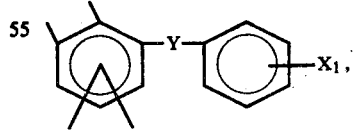 (XXIIIa)

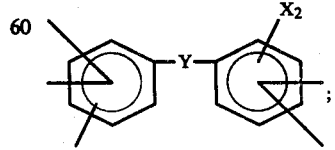 (XXIIIb)

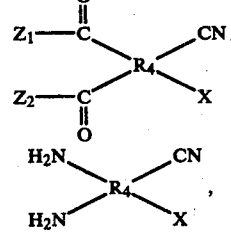 (XXIV)

or without a nitrile if prepolymer (XX) is to be made, wherein n is an integer from 0 to 30, depending on the chemical structural formula or the solubility of the aromatic nitrile-modified prepolymer in organic solvents; $n_1$ is either 0 or greater than 1, $n_2$ is a positive integer greater than 1, and sum of $n_1$ and $n_2$ is an integer from 1 to 50;

$R_1$ and $R_4$ are aryl radicals, heterocyclic radicals, particularly those heterocyclic radicals containing one, two or three nitrogen atoms in the ring, or combination of both aryl and heterocyclic radicals; in prepolymer (XX), $R_1$ in the brackets followed by the subscript $n_1$ cannot contain a nitrile group, whereas $R_1$ in the brackets followed by the subscript $n_2$ must contain a nitrile group; and in the preferred embodiments $R_1$ is a tetravalent aromatic radical selected from the group consisting of:

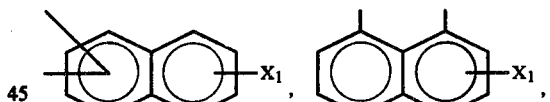

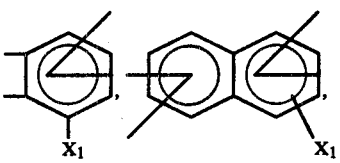

nitrile (XXIIIa) is an aromatic nitrile selected from the group consisting of:

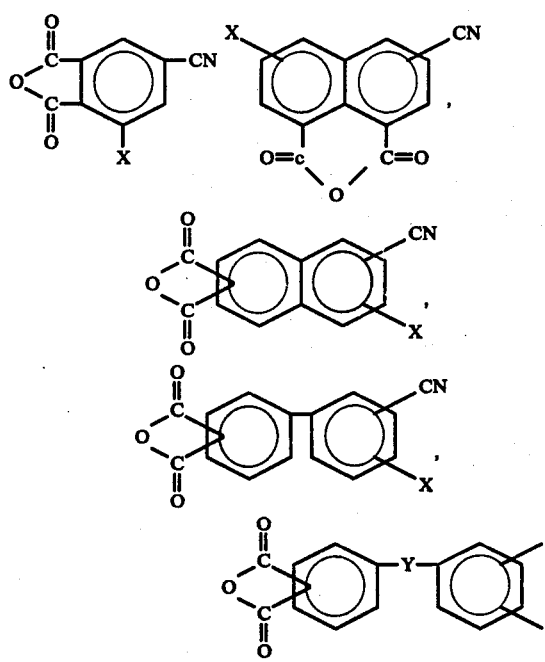

nitrile (XXIIIb) is the derivative of aromatic nitrile (XXIIIa), wherein the dicarboxylic acid anhydride moiety becomes either a diacid, a diester, a halfester or a dicarbonyl halide having the two carboxyl or carbonyl groups in the ortho positions on the aryl ring; nitrile (XXIV) is an aromatic nitrile selected from the group consisting of:

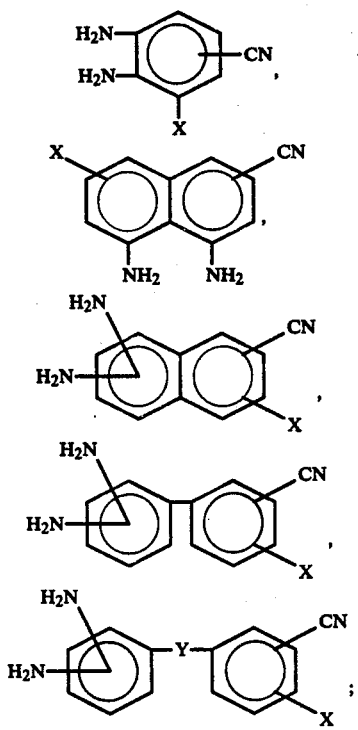

$X_1$ and $X_2$ are monovalent radicals selected from the group consisting of —H, —CN, —F, —Cl, —Br, —NO$_2$, —CH$_3$, and

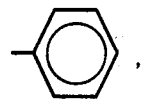

where $X_1$ may or may not be the same group as $X_2$, and X may be either $X_1$ or $X_2$; Y is a bivalent radical selected from the group consisting of:

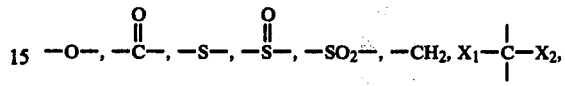

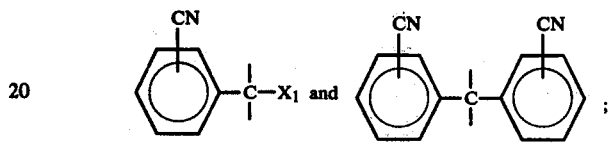

and $Z_1$ and $Z_2$ are monovalent radicals selected from the group consisting of: hydroxyl, alkyoxyls, aroxyls, and halides, where $Z_1$ may or may not be the same group as $Z_2$, and Z may be either $Z_1$ or $Z_2$.

13. An imidazopyrrolone prepolymer of claim 12 wherein the tetracarboxylic acid dianhydride (XXIa), or its derivatives (XXIb) are selected from the group consisting of:

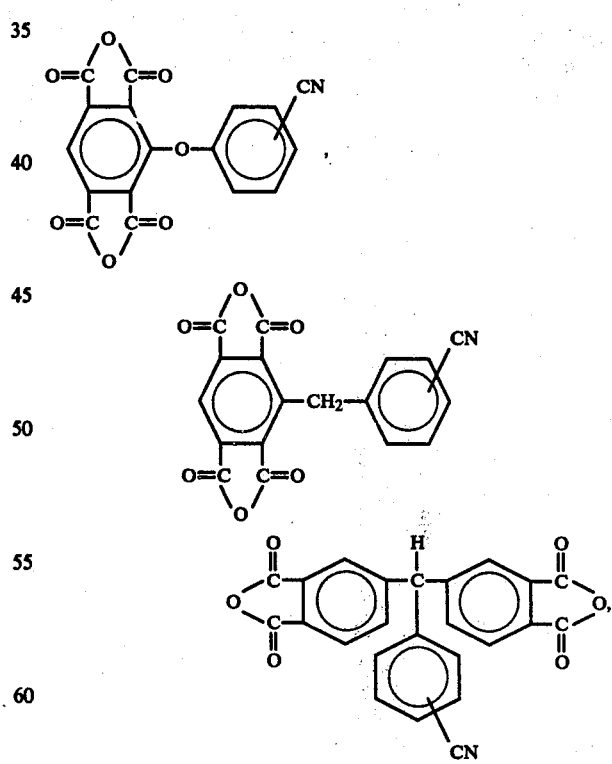

and their ester and halide derivatives, respectively.

14. An imidazopyrrolone prepolymer of claim 12 wherein the tetraamine (XXII) is selected from the group consisting of:

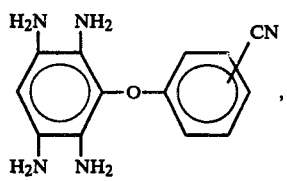,

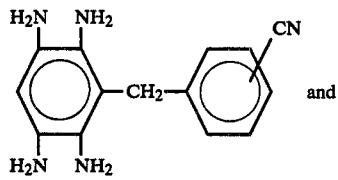 and

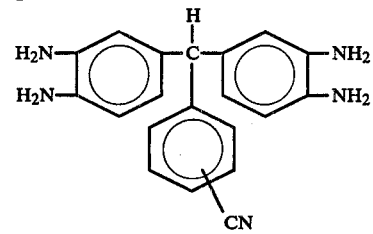

15. An imidazopyrrolone prepolymer of claim 12 wherein n is zero.

16. A triazine ring containing or cross-linked polymer composition made by catalytically trimerizing an aromatic nitrile-modified imidazopyrrolone prepolymer of claim 12.

17. The polymer composition of claim 16 which is catalytically trimerized in the presence of reinforcing filler material.

18. An aromatic nitrile-modified (terminated and/or appended) quinoxaline prepolymer having one of the following four general structural formulas:

which is the reaction product of a diglyoxal having the structural formula:

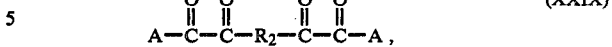 (XXIX)

a tetra-amine having the structural formula:

 (XXX)

with a nitrile having one of the following structural formulas, if prepolymer (XXV), (XXVI) or (XXVII) is to be made:

 (XXXI)

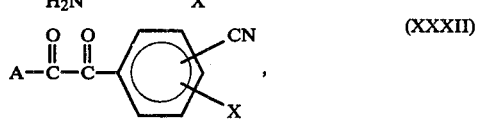 (XXXII)

or without a nitrile if prepolymer (XXVIII) is to be made, wherein n is an integer from 0 to 100, depending on the chemical structural formula or the solubility of the aromatic nitrile-modified prepolymer in organic solvents; $n_1$ is either 0 or greater than 1, $n_2$ is a positive integer greater than 1, and the sum of $n_1$ and $n_2$ is an integer from 1 to 100;

$R_1$, $R_2$, and $R_4$ are aryl radicals, heterocyclic radicals, particularly those heterocyclic radicals containing one, two, or three nitrogen atoms in the ring, or a

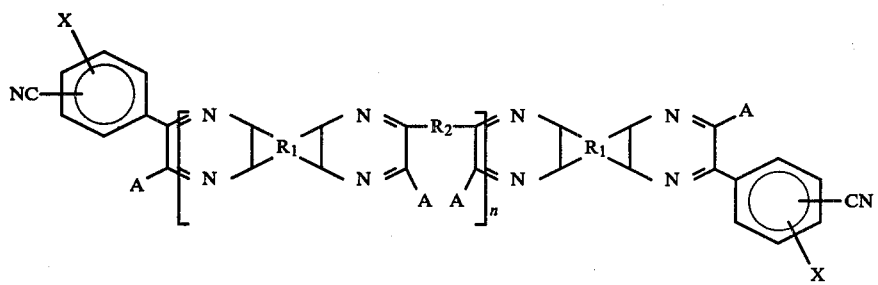 (XXV)

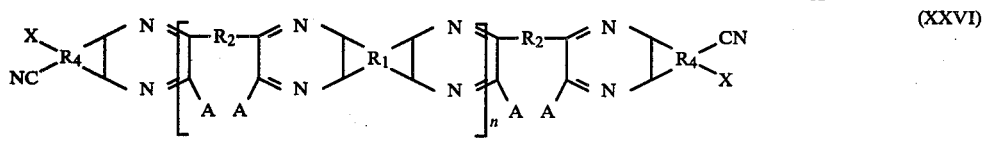 (XXVI)

(XXVII)

(XXVIII)

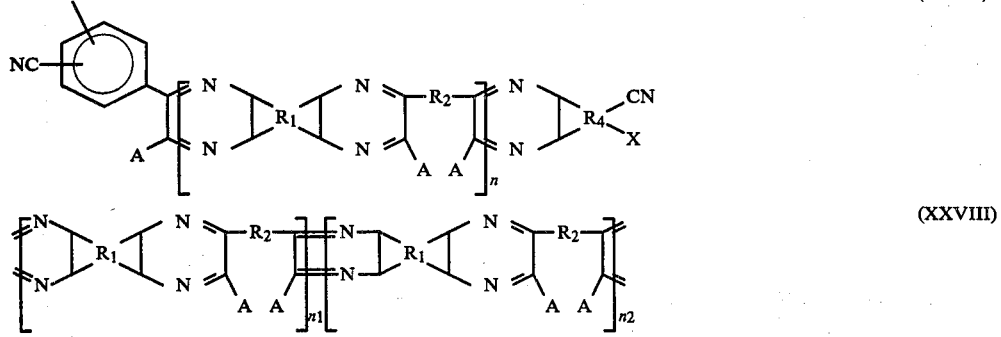

combination of both aryl and heterocyclic radicals; in prepolymer (XXVIII), $R_1$ and $R_2$ in the brackets followed by the subscript $n_2$ must contain a nitrile group; and in the preferred embodiments $R_1$ is a tetravalent aromatic radical selected from the group consisting of:

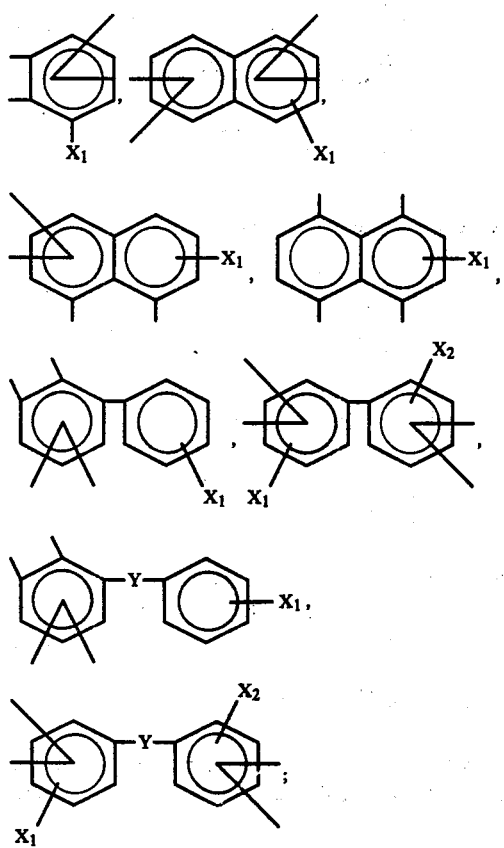

$R_2$ is a bivalent aromatic radical selected from the group consisting of:

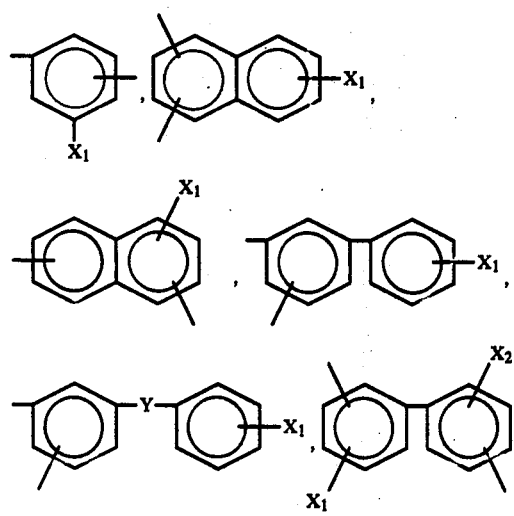

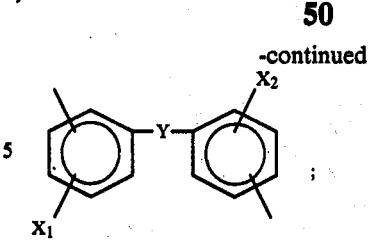

nitrile (XXXI) is an aromatic nitrile selected from the group consisting of:

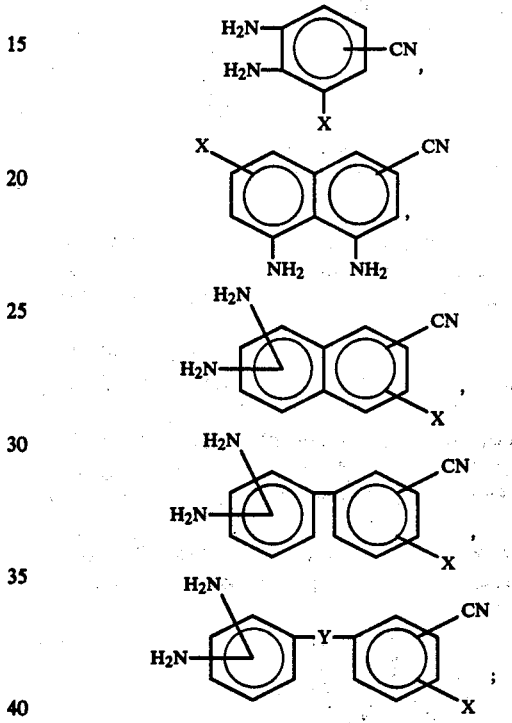

$X_1$ and $X_2$ are monovalent radicals selected from the group consisting of —H, —CN, —F, —Cl, —Br, —NO$_2$, —CH$_3$, and

where $X_1$ may or may not be the same group as $X_2$, and X may be either $X_1$ or $X_2$;

Y is a bivalent radical selected from the group consisting of:

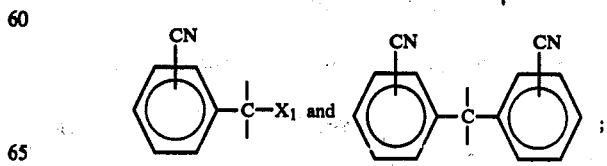

and A is a monovalent radical selected from the group consisting of:

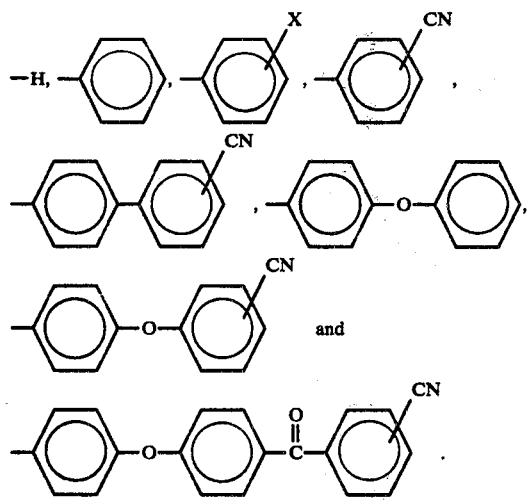

19. A triazine ring containing or cross-linked polymer composition made by catalytically trimerizing an aromatic nitrile-modified quinoxaline prepolymer of claim 18.

20. The polymer composition of claim 19 which is catalytically trimerized in the presence of reinforcing filler material.

21. An aromatic nitrile-modified (terminated and/or appended) precopolymer made by combining two, three or four of the following groups of monomeric reactants:

(A) a tetracarboxylic acid dianhydride (Va) or its derivatives (Vb) having the structural formulas:

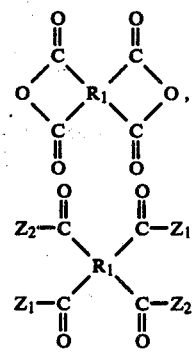

and a diamine having the structural formula:

(VI) H$_2$N—R$_2$—NH$_2$;

(B) a dicarboxylic acid or its derivatives having the structural formula:

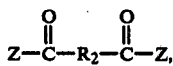

and a tetra-amine having the structural formula:

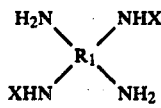

(C) a tetracarboxylic acid dianhydride (XXIa) or its derivatives (XXIb) having the structural formulas:

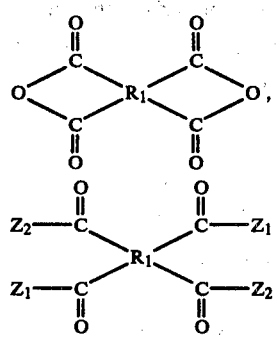

and a tetra-amine having the structural formula:

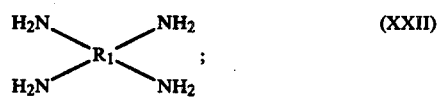

(D) a diglyoxal having the structural formula:

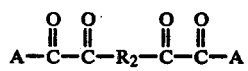

and a tetra-amine having the structural formula:

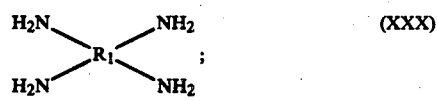

with or without one or more appropriate terminating nitrile reagents having the following structural formulas:

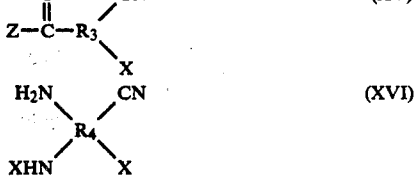

-continued

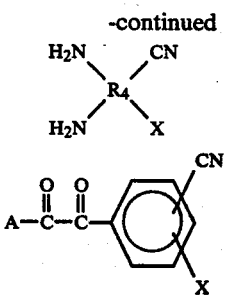
(XXIV)

(XXXII)

wherein

R₁, R₂, R₃ and R₄ are aryl radicals, heterocyclic radicals, particularly those heterocyclic radicals containing one, two or three nitrogen atoms in the ring, or a combination of both aryl and heterocyclic radicals; and in the preferred embodiment R₁ is a tetravalent aromatic radical selected from the group consisting of:

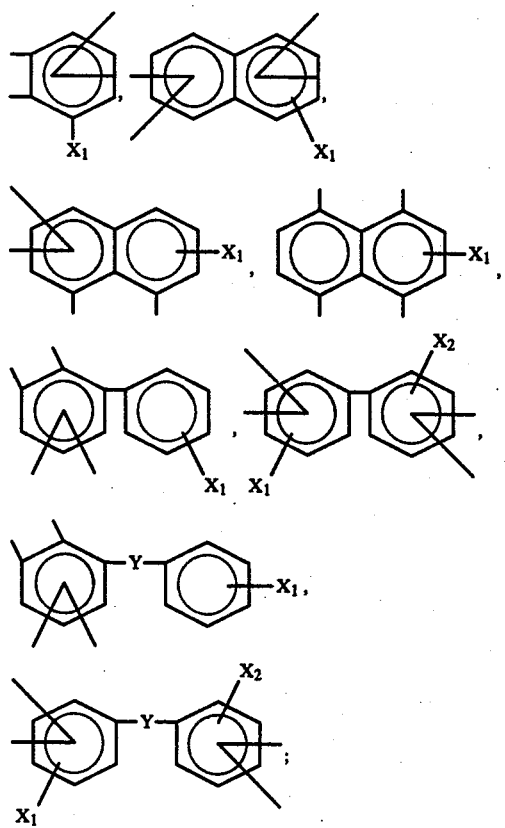

R₂ is a bivalent aromatic radical selected from the group consisting of:

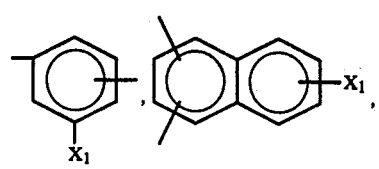

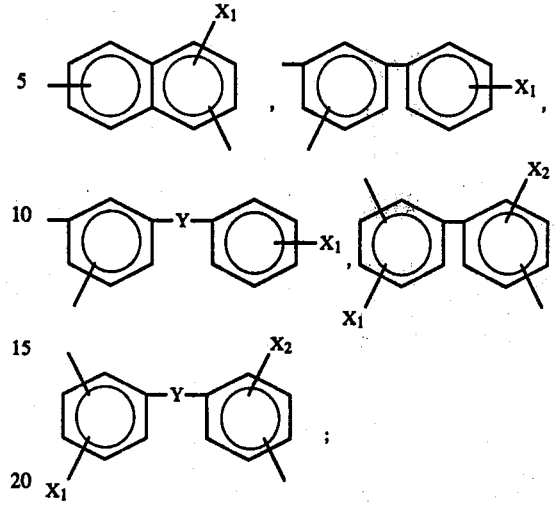

nitrile (VII) is an aromatic nitrile selected from the group consisting of:

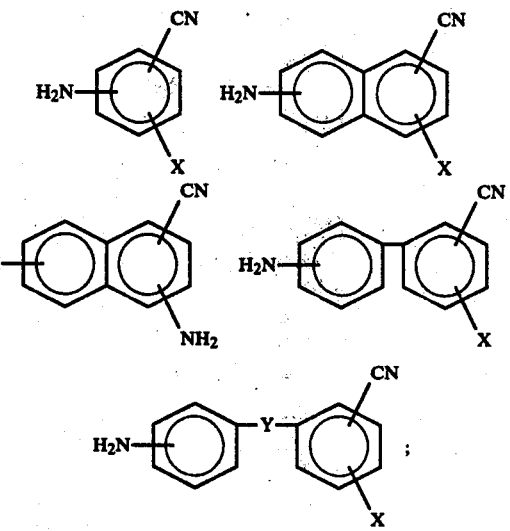

nitrile (VIIIa) is an aromatic nitrile selected from the group consisting of:

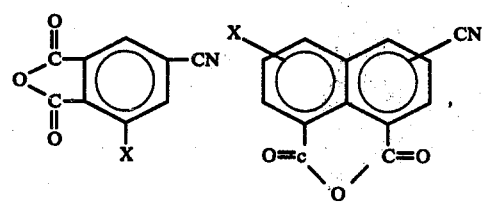

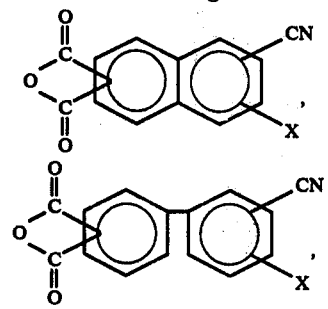

-continued

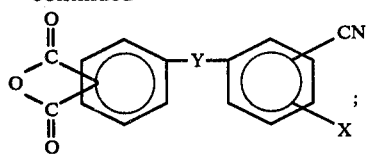

nitrile (VIIIb) is the derivative of aromatic nitrile (VIIIa), wherein the dicarboxylic acid anhydride moiety becomes either a diacid, a diester, a halfester or a dicarbonyl halide having the two carboxyl or carbonyl groups in the ortho positions on the aryl ring;

nitrile (XV) is an aromatic nitrile selected from the group consisting of:

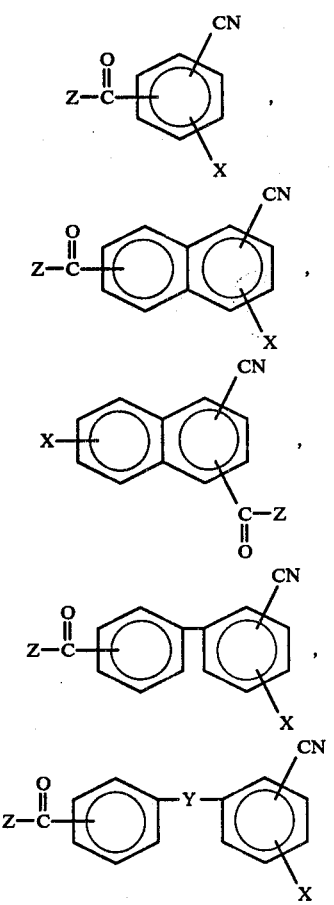

nitrile (XVI) is an aromatic nitrile selected from the group consisting of:

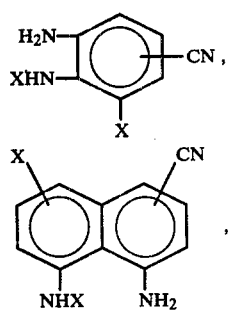

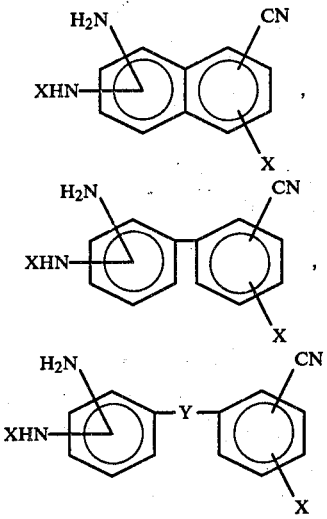

nitrile (XXIV) is an aromatic nitrile selected from the group consisting of:

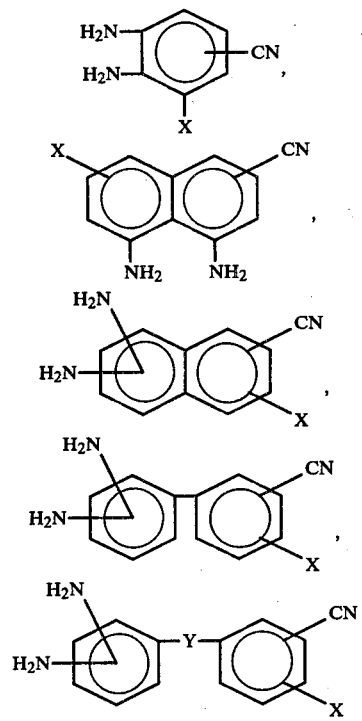

$X_1$ and $X_2$ are monovalent radicals selected from the group consisting of —H, —CN, —F, —Cl, —Br, —NO$_2$, —CH$_3$, and

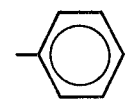

where $X_1$ may or may not be the same group as $X_2$, and X may be either $X_1$ or $X_2$;

Y is a bivalent radical selected from the group consisting of:

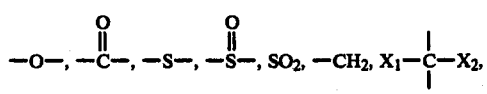

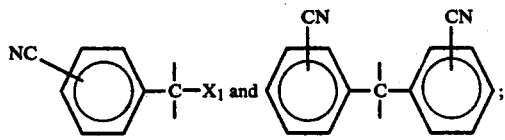

$Z_1$ and $Z_2$ are monovalent radicals selected from the group consisting of: hydroxyl, alkyoxyls, aroxyls, and halides, where $Z_1$ may or may not be the same group as $Z_2$, and may be either $Z_1$ or $Z_2$ and A is a monovalent radical selected from the group consisting of:

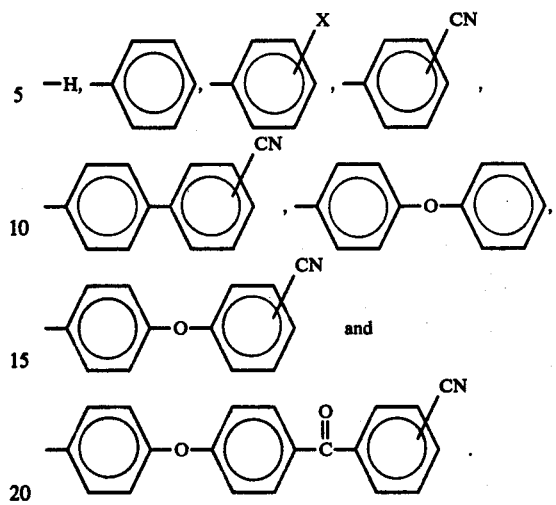

22. A triazine ring containing or cross-linked copolymer composition made by catalytically trimerizing an aromatic nitrile-modified precopolymer of claim 21.

23. The copolymer composition of claim 22 which is catalytically trimerized in the presence of reinforcing filler material.

* * * * *